(12) United States Patent
Althorpe et al.

(10) Patent No.: US 10,531,692 B2
(45) Date of Patent: *Jan. 14, 2020

(54) DISPOSABLE CARTRIDGE FOR USE IN AN ELECTRONIC NICOTINE DELIVERY SYSTEM

(71) Applicant: McNeil AB, Helsingborg (SE)

(72) Inventors: Christopher Althorpe, Cardiff (GB); Ian James Binder, Wiltshire (GB); David Andrew McLeod, Bristol (GB); Lee Kelepouris, Helsingborg (SE); Salih Muhsin Muhammed, Hyllinge (SE); Johan Nordström, Helsingborg (SE); Alexandru Paunescu, Clinton, NJ (US)

(73) Assignee: McNeil AB, Helsingborg (SE)

(*) Notice: Subject to any disclaimer, the term of this patent is extended or adjusted under 35 U.S.C. 154(b) by 0 days.

This patent is subject to a terminal disclaimer.

(21) Appl. No.: 16/257,215

(22) Filed: Jan. 25, 2019

(65) Prior Publication Data

US 2019/0150514 A1 May 23, 2019

Related U.S. Application Data

(63) Continuation of application No. 15/525,640, filed as application No. PCT/EP2015/076879 on Nov. 17, 2015, now Pat. No. 10,226,076.

(Continued)

(51) Int. Cl.
*A24F 13/00* (2006.01)
*A24F 47/00* (2006.01)
(Continued)

(52) U.S. Cl.
CPC .......... *A24F 47/008* (2013.01); *A61M 15/06* (2013.01); *A61M 11/042* (2014.02)

(58) Field of Classification Search
CPC ..... A24F 47/008; A24F 47/002; A61M 15/06; H05B 3/44
(Continued)

(56) References Cited

U.S. PATENT DOCUMENTS

| 3,520,629 A | 7/1970 | Otsuka Katsumi |
| 4,274,479 A | 6/1981 | Eastman |

(Continued)

FOREIGN PATENT DOCUMENTS

| CN | 201238609 Y | 5/2009 |
| CN | 203709256 U | 7/2014 |

(Continued)

OTHER PUBLICATIONS

Adkison et al., "Electronic Nicotine Delivery Systems: International Tobacco Control Four-Country Survey," *American Journal of Preventive Medicine*, vol. 44, Issue 3, pp. 207-215 (Mar. 2013).

(Continued)

*Primary Examiner* — Hae Moon Hyeon

(57) ABSTRACT

A novel disposable cartridge for use in an electronic nicotine delivery system having an electric heater includes a reservoir containing a nicotine-containing liquid, a port in liquid communication with the reservoir, a liquid barrier disposed proximate the port to prevent undesired leakage of the nicotine-containing liquid from the reservoir, and a durable, elongate wick arranged and configured to be slideable in the port and to contact the nicotine-containing liquid in the reservoir.

7 Claims, 31 Drawing Sheets

Related U.S. Application Data

(60) Provisional application No. 62/080,666, filed on Nov. 17, 2014.

(51) Int. Cl.
*A61M 15/06* (2006.01)
*A61M 11/04* (2006.01)

(58) Field of Classification Search
USPC .................................................. 131/328, 329
See application file for complete search history.

(56) References Cited

U.S. PATENT DOCUMENTS

| | | | |
|---|---|---|---|
| 5,322,075 A | 6/1994 | Deevi et al. | |
| 5,408,574 A | 4/1995 | Deevi et al. | |
| 5,498,855 A | 3/1996 | Deevi et al. | |
| 5,750,964 A | 5/1998 | Counts et al. | |
| 8,156,944 B2 | 4/2012 | Han | |
| 8,299,405 B2 | 10/2012 | Ireman et al. | |
| 10,188,148 B2 * | 1/2019 | Althorpe | A24F 47/008 |
| 10,226,076 B2 * | 3/2019 | Althorpe | A24F 47/008 |
| 2003/0075188 A1 * | 4/2003 | Adiga | A24F 47/004 |
| | | | 131/185 |
| 2010/0181387 A1 | 7/2010 | Zaffaroni et al. | |
| 2011/0048682 A1 | 3/2011 | Yu et al. | |
| 2012/0006342 A1 | 1/2012 | Rose et al. | |
| 2012/0255567 A1 | 10/2012 | Rose et al. | |
| 2013/0081642 A1 | 4/2013 | Safari | |
| 2013/0160764 A1 | 6/2013 | Liu | |
| 2013/0192615 A1 | 8/2013 | Tucker et al. | |
| 2013/0340750 A1 | 12/2013 | Thorens et al. | |
| 2013/0340775 A1 | 12/2013 | Juster et al. | |
| 2014/0014126 A1 | 1/2014 | Peleg et al. | |
| 2014/0020693 A1 | 1/2014 | Cochand et al. | |
| 2014/0109921 A1 | 4/2014 | Chen | |
| 2014/0130816 A1 | 5/2014 | Liu | |
| 2014/0144429 A1 | 5/2014 | Wensley et al. | |
| 2014/0150784 A1 | 6/2014 | Liu | |
| 2014/0190496 A1 | 7/2014 | Wensley et al. | |
| 2014/0209105 A1 | 7/2014 | Sears et al. | |
| 2014/0238422 A1 | 8/2014 | Plunkett et al. | |
| 2014/0283855 A1 | 9/2014 | Hawes et al. | |
| 2014/0318558 A1 | 10/2014 | Liu | |
| 2014/0346689 A1 | 11/2014 | Dubief | |
| 2015/0083147 A1 | 3/2015 | Schiff et al. | |
| 2015/0090279 A1 | 4/2015 | Chen | |
| 2015/0264979 A1 | 9/2015 | Thorens et al. | |
| 2015/0289567 A1 | 10/2015 | Liu | |
| 2016/0000147 A1 | 1/2016 | Li et al. | |
| 2016/0029698 A1 | 2/2016 | Xiang | |
| 2016/0120222 A1 | 5/2016 | Bagai et al. | |
| 2016/0135505 A1 | 5/2016 | Li et al. | |
| 2016/0143365 A1 | 5/2016 | Liu | |
| 2016/0183596 A1 | 6/2016 | Rado | |
| 2017/0119055 A1 * | 5/2017 | Liu | A24F 47/008 |
| 2017/0231286 A1 | 8/2017 | Borkovec et al. | |
| 2017/0360092 A1 | 12/2017 | Althorpe et al. | |
| 2017/0367402 A1 | 12/2017 | Lau et al. | |

FOREIGN PATENT DOCUMENTS

| | | |
|---|---|---|
| CN | 203828069 U | 9/2014 |
| CN | 203828073 U | 9/2014 |
| CN | 203828084 U | 9/2014 |
| CN | 104126873 A | 11/2014 |
| EP | 503767 A | 9/1992 |
| EP | 2113178 A | 11/2009 |
| EP | 2340729 A | 7/2011 |
| EP | 2460424 A | 6/2012 |
| EP | 2606756 A | 6/2013 |
| GB | 2471453 A | 1/2011 |
| GB | 2504076 A | 1/2014 |
| GB | 2513638 A | 11/2014 |
| JP | 2005-106313 A | 4/1998 |
| KR | 101293857 B | 8/2013 |
| KR | 101293859 B | 8/2013 |
| RU | 103281 U1 | 4/2011 |
| WO | WO 1997/24966 A | 7/1997 |
| WO | WO 1998/16262 A | 4/1998 |
| WO | WO 2010/073018 A | 7/2010 |
| WO | WO 2011/146375 A | 11/2011 |
| WO | WO 2013/083634 A | 6/2013 |
| WO | WO 2013/083635 A | 6/2013 |
| WO | WO 2013/083636 A | 6/2013 |
| WO | WO 2013/083638 A | 6/2013 |
| WO | WO 2013/098395 A | 7/2013 |
| WO | WO 2014/012894 A | 1/2014 |
| WO | WO 2014/139609 A | 9/2014 |
| WO | WO 2014/139610 A | 9/2014 |
| WO | WO 2014/187770 A | 11/2014 |
| WO | WO 2016/079151 A | 5/2016 |
| WO | WO 2016/079152 A | 5/2016 |
| WO | WO 2016/079155 A | 5/2016 |

OTHER PUBLICATIONS

International search report and Written Opinion dated May 4, 2016, for PCT/EP2015/076883.
International search report and Written Opinion dated Feb. 29, 2016, for PCT/EP2015/076879.

\* cited by examiner

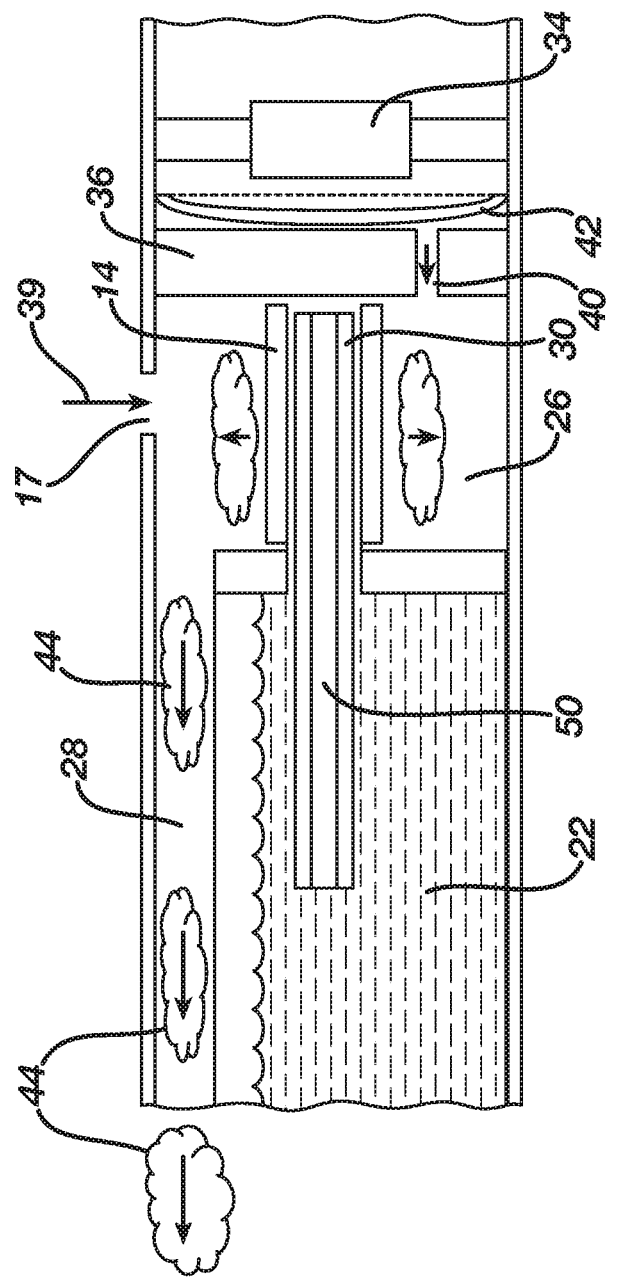

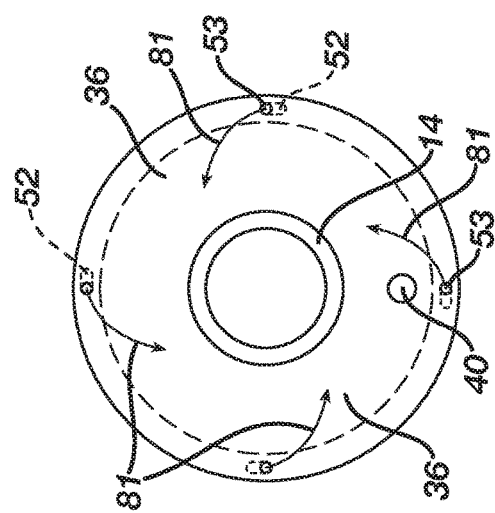
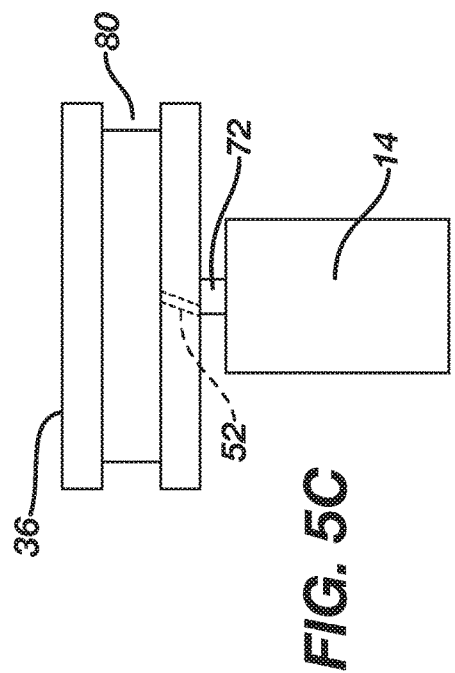
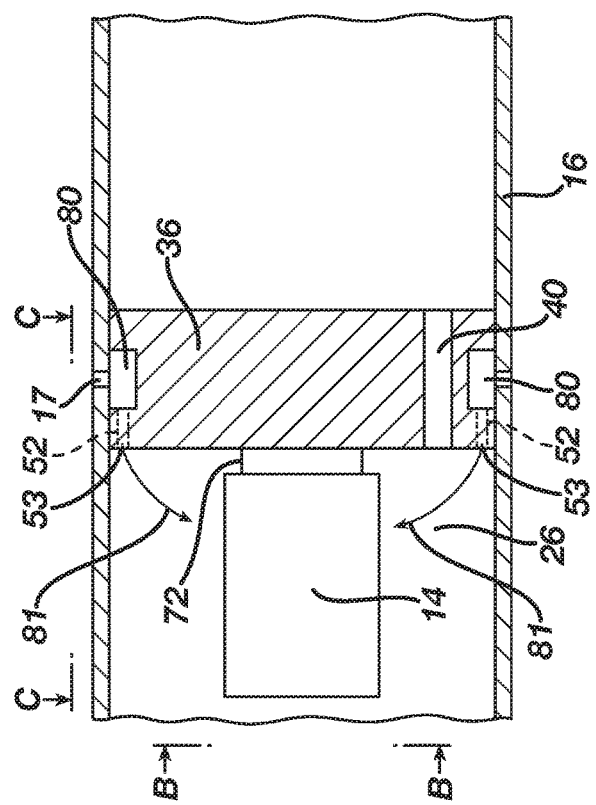
FIG. 5B
FIG. 5C
FIG. 5A

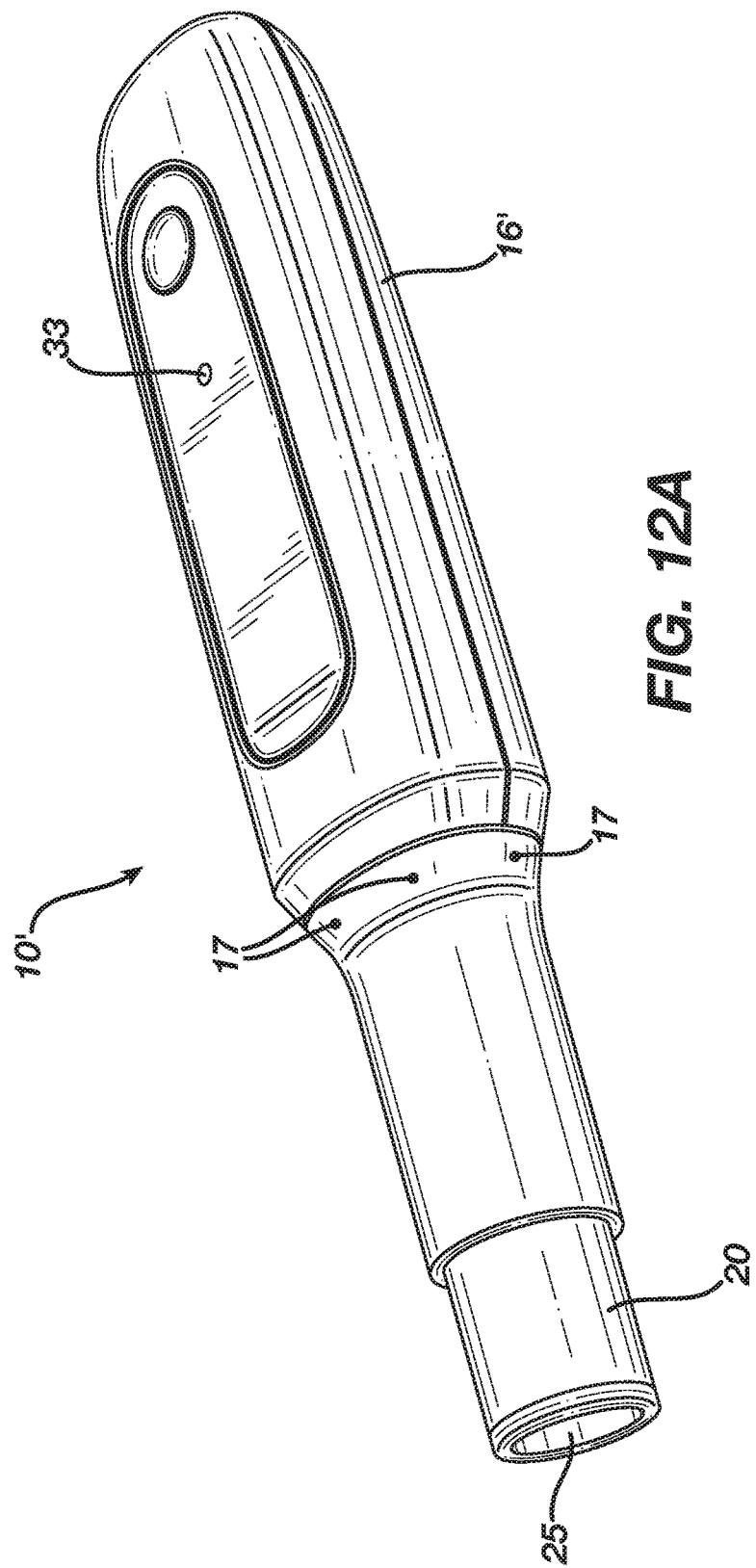

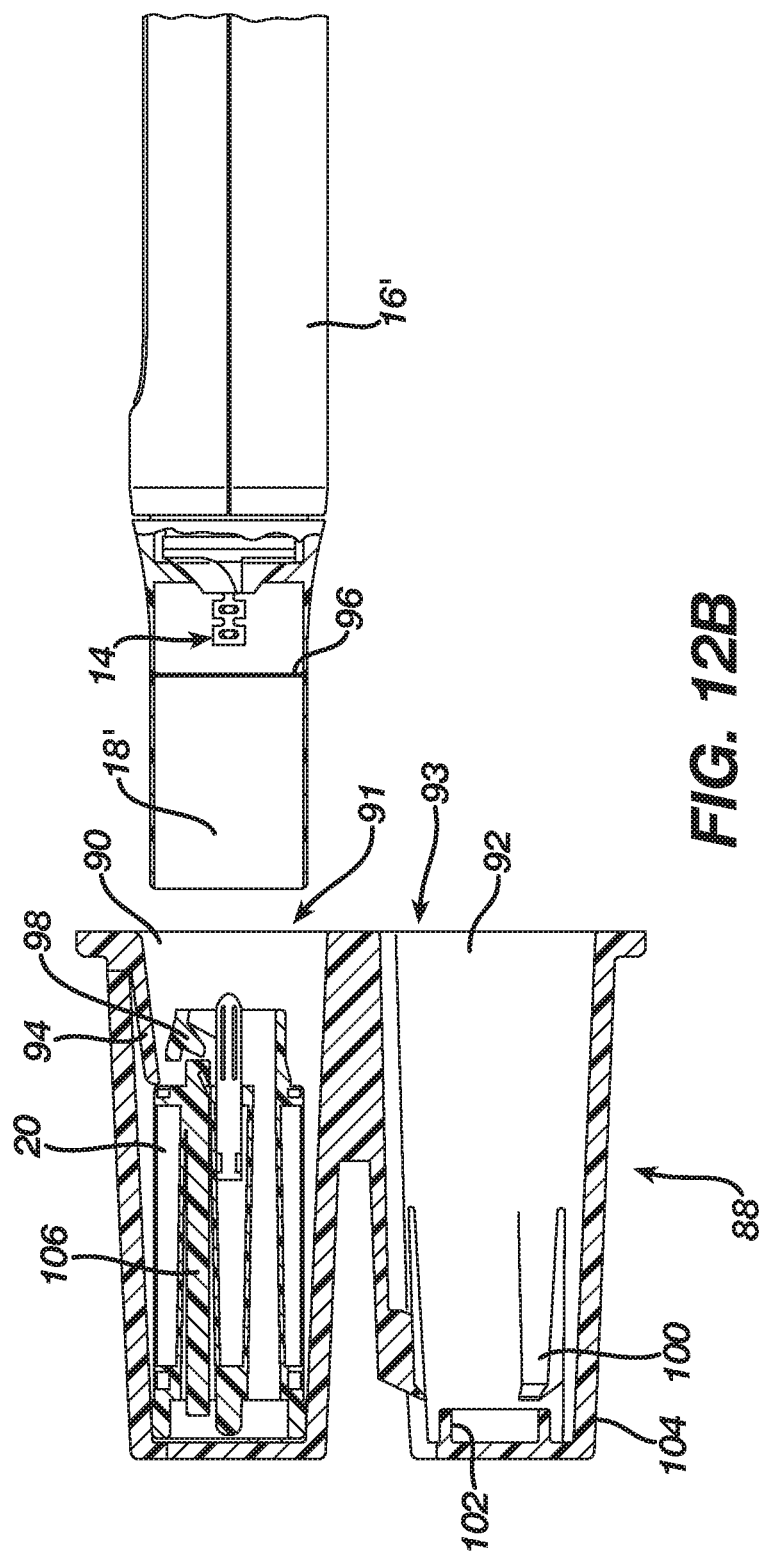

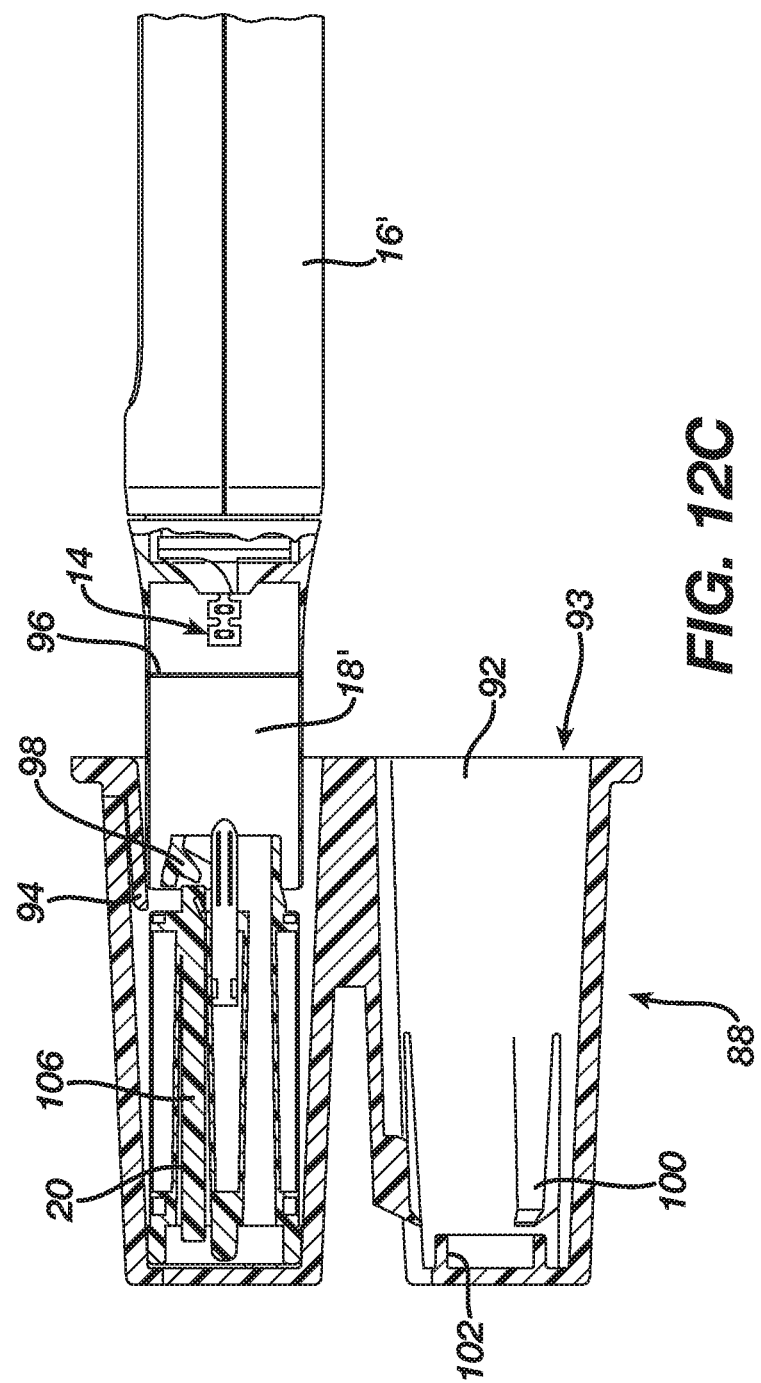

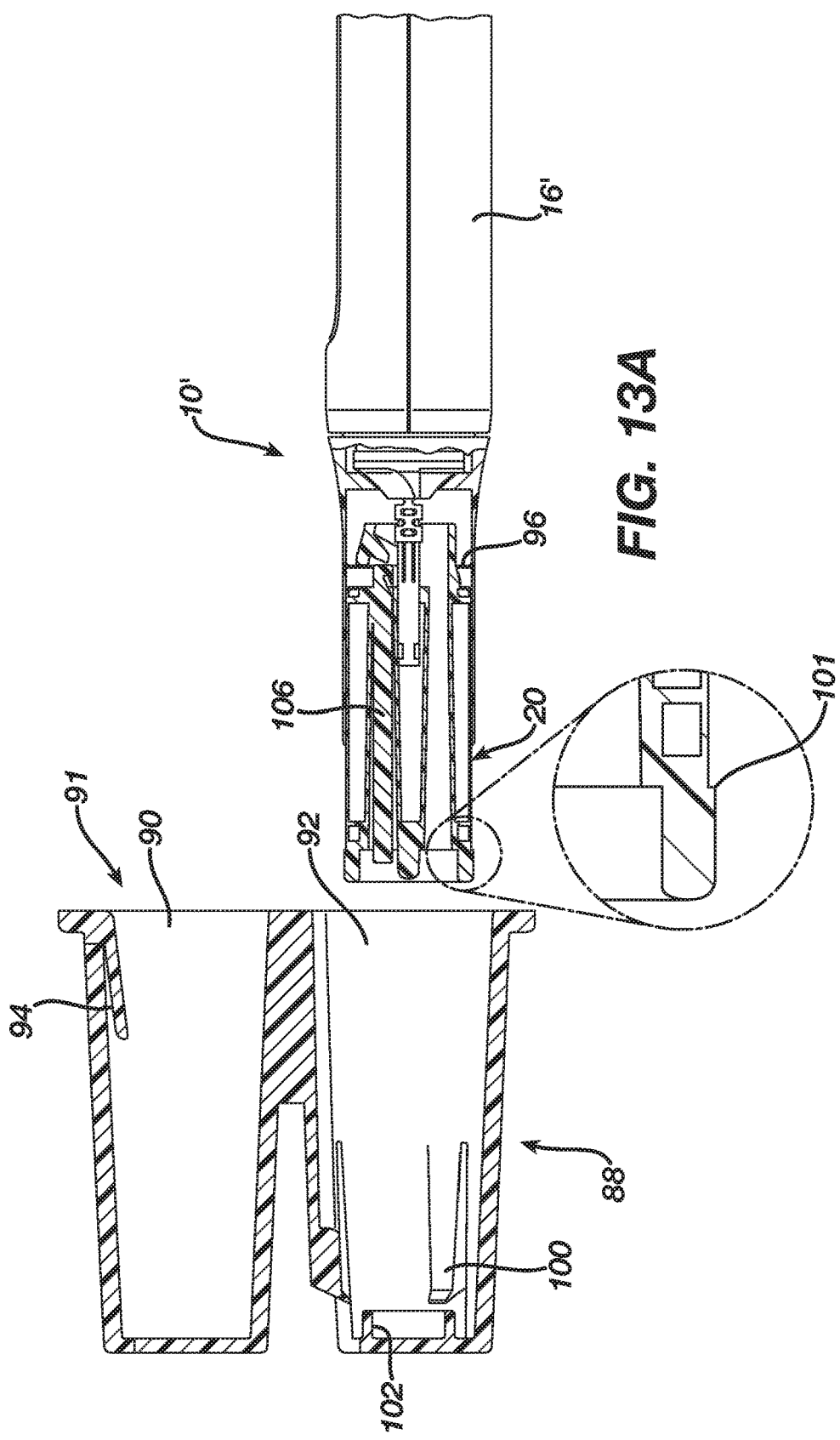

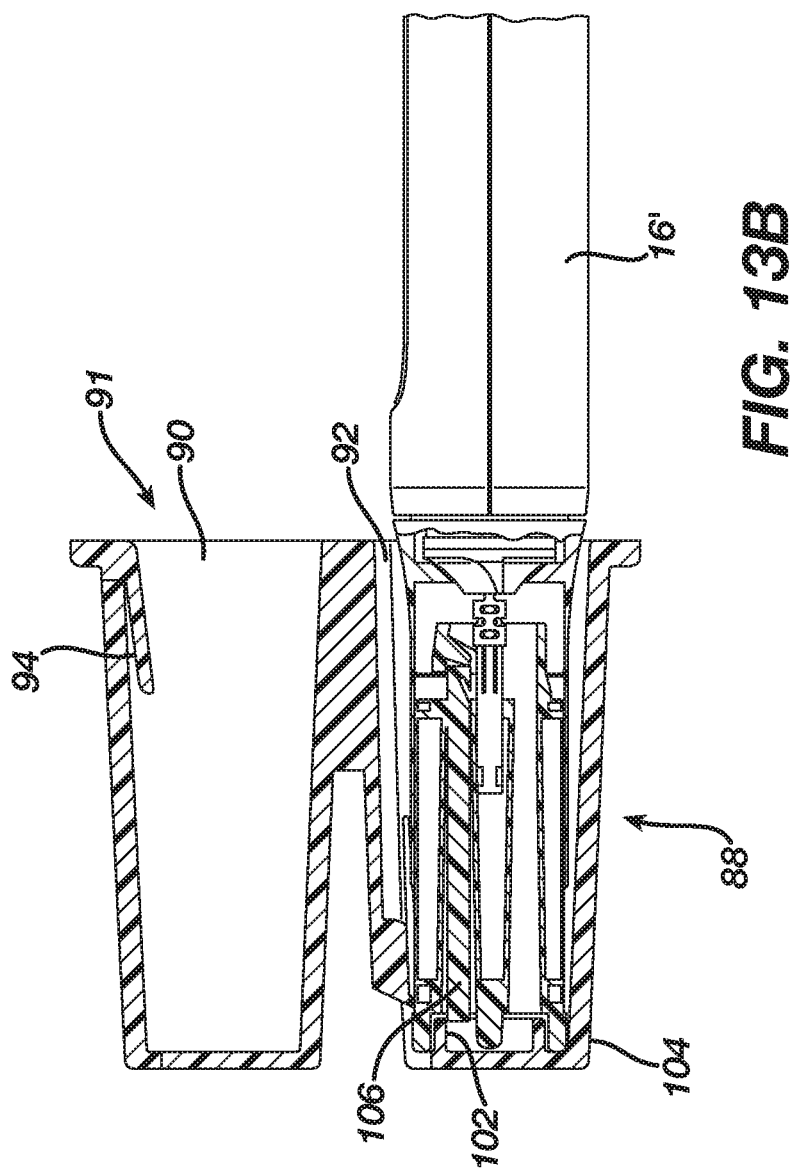

DISPOSABLE CARTRIDGE FOR USE IN AN ELECTRONIC NICOTINE DELIVERY SYSTEM

CROSS-REFERENCE TO RELATED APPLICATIONS

This application is a continuation of U.S. application Ser. No. 15/525,640 filed on May 10, 2017, which is the national stage filing under 35 USC 371 of international application PCT/EP2015/076879 filed on Nov. 17, 2015, which claims priority to U.S. provisional application 62/080,666 filed on Nov. 17, 2014, the complete disclosures of which are hereby incorporated herein by reference for all purposes.

FIELD OF THE INVENTION

The present invention relates to a system for the delivery of a nicotine aerosol to a human, components thereof, and methods of using the system. In particular, the invention relates to a disposable cartridge for use in such systems and kits including such a disposable cartridge.

DESCRIPTION OF THE PRIOR ART

Electronic nicotine delivery systems (ENDS) emerged in 2003 and have grown to become widely available globally ("Electronic Nicotine Delivery Systems: International Tobacco Control Four-Country Survey," *American Journal of Preventive Medicine*, VOL. 44, Issue 3, pp. 207-215 (March 2013)). These systems replace conventional smoking articles that involve the combustion of tobacco or other smokable material. The ENDS generally involve the vaporization and/or aerosolization of nicotine, often by heating a nicotine-containing liquid to mimic conventional smoking without combustion and generating tar and some of the more dangerous byproducts of conventional smoking articles.

Some inexpensive products, known as e-cigarettes, on the market deliver the nicotine-containing liquid to the heater via a fabric saturated with the liquid (Rose et al., US Pat. App. Pub. No. US2012/0255567 A1). Other devices provide a disposable cartridge for the liquid (Philip Morris Products S.A., Eur. Pat. App Pub. No. EP 2 113 178 A1). In some such products, the liquid saturates a sponge material that helps to transport it to the heater. Other systems incorporate an inexpensive glass fiber bundle wick to transport the liquid from the heater (Philip Morris Products, S.A., Eur. Pat. App. Pub. No. EP2 606 756 A1). The wick itself is often integrated with an electric heater (Tucker et al., US Pat. App. Pub. No. US2013/0192615 A1). Thus, the liquid, wick and heater are all elements of the disposable cartridge. The combination of the wick and heater in the disposable cartridge tends to result in low cost, bare wire heaters wrapped around the wick to minimize cost in the disposable components.

There have also been attempts to use the e-cigarette technology for actual smoking cessation regimens and/or nicotine replacement therapy. Examples of these uses are disclosed in Rose et al., US Pat. App. Pub. No. US2012/0255567 A1; and Juster et al., US Pat. App. Pub. No. US2013/0340775A1; and Wensley et al., US Pat. App. Pub. No. US 2014/0144429 A1.

SUMMARY OF THE INVENTION

Surprisingly, we have found a novel disposable cartridge for use in an electronic nicotine delivery system having an electric heater. The disposable cartridge includes a reservoir containing a nicotine-containing liquid, a port in liquid communication with the reservoir, a liquid barrier disposed proximate the port to prevent undesired leakage of the nicotine-containing liquid from the reservoir, and a durable, elongate wick arranged and configured to be slideable in the port and to contact the nicotine-containing liquid in the reservoir.

Another embodiment of the invention relates to a kit for use in an electronic nicotine delivery system having an electric heater. The kit includes a disposable cartridge and a durable, elongate wick. The disposable cartridge has a reservoir containing a nicotine-containing liquid, a port in liquid communication with the reservoir, and a liquid barrier disposed proximate the port to prevent undesired leakage of the nicotine-containing liquid from the reservoir. The durable, elongate wick is slidably insertable into the port to disrupt the liquid barrier to permit liquid interaction between the solid, elongate wick and the nicotine-containing liquid in the reservoir.

BRIEF DESCRIPTION OF THE DRAWINGS

FIGS. 4A-4G are schematic views of the movement of air through an ENDS, the formation of a nicotine aerosol, and the movement of the aerosol toward a mouthpiece of an ENDS.

FIG. 5A is a schematic cross section of an electric heater and baseplate useful in an ENDS of the present invention.

FIG. 5B is an end view of the electric heater and baseplate of FIG. 5A.

FIG. 5C is a top view of the electric heater and baseplate of FIG. 5A.

FIG. 12A is a perspective view of an alternative embodiment of the ENDS of the present invention.

FIGS. 12B-E are cross-sections of the ENDS of FIG. 12A and a container during the loading of a disposable cartridge into the receptacle of the ENDS housing.

FIGS. 13A-C are cross-sections of the ENDS and a container during the unloading of a disposable cartridge from the receptacle of the ENDS housing.

DETAILED DESCRIPTION OF THE PREFERRED EMBODIMENTS

A more particular description of the invention, briefly summarized above may be had by reference to the embodiments thereof that are illustrated in the appended drawings. It is to be so noted, however, that the appended drawings illustrate only typical embodiments of the invention and, therefore, are not to be considered limiting of its scope, for the invention may admit to other equally effective embodiments.

As used herein the specification and the claims, the term "non-porous" and variants thereof relate to a solid physical structure that is capable of interaction with liquid without ingress of such liquids into the solid structure. This can be achieve, for example, with a solid structure that simply has no pores to permit liquid ingress or by altering the surface of an otherwise porous structure with an impermeable coating material or a surface treatment that essentially closes surface pores. Substantially all fluid transport along such a structure occurs on the outer surfaces thereof, not through the structure, itself.

As used herein the specification and the claims, the term "thermal degradation" and variants thereof relate to damage or destruction in the presence of elevated temperatures. This includes combustion, charring, melting, deformation, destruction, off-gassing of toxic or other dangerous substances, and the like.

As used herein the specification and the claims, the term "durable" and variants thereof relate to the ability of a structure to resist damage, wear, friability, distortion, buckling, and/or destruction while being subjected to friction during sliding motions along adjacent structures and into interference fittings.

Figure 1:
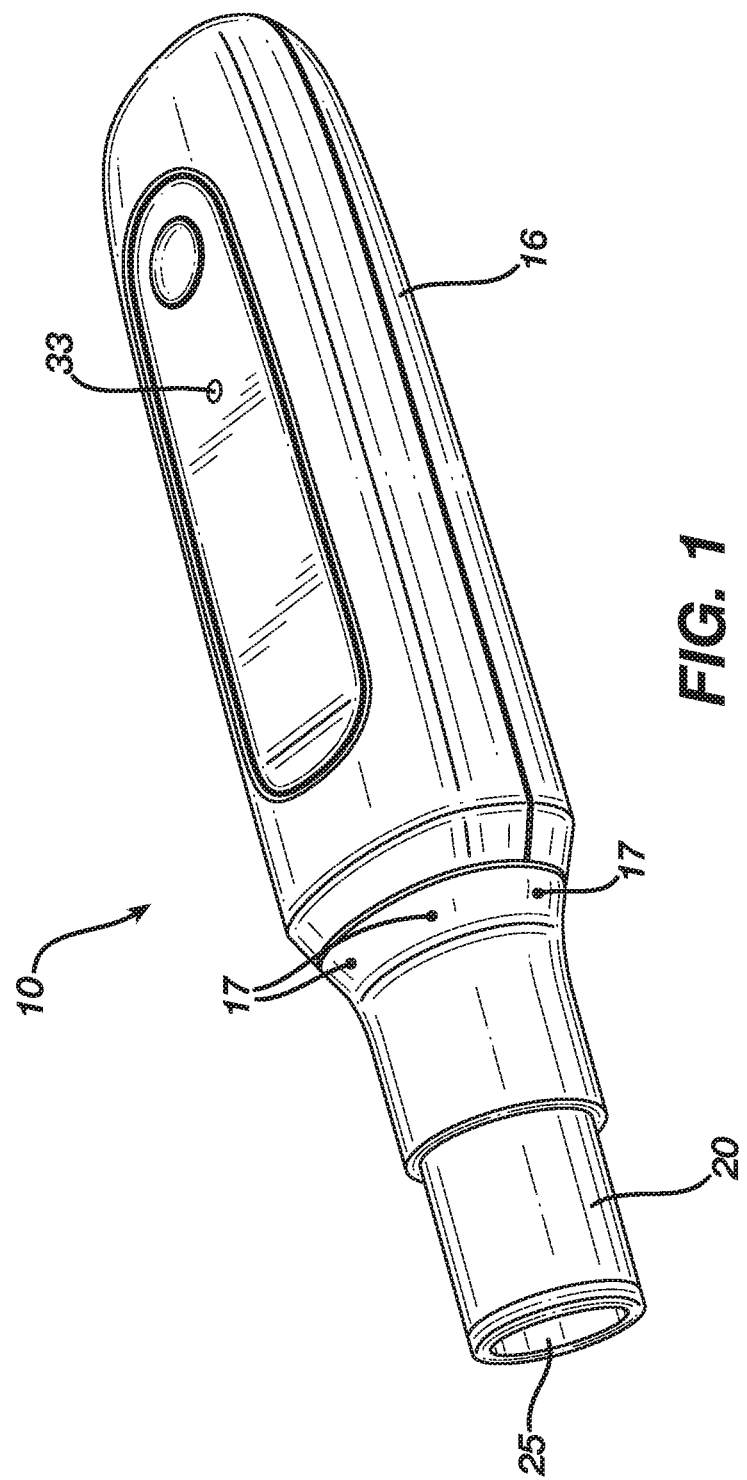
FIG. 1 is a perspective view of an assembled electronic nicotine delivery system ("ENDS") according to one embodiment of the present invention.
Figure 2A:
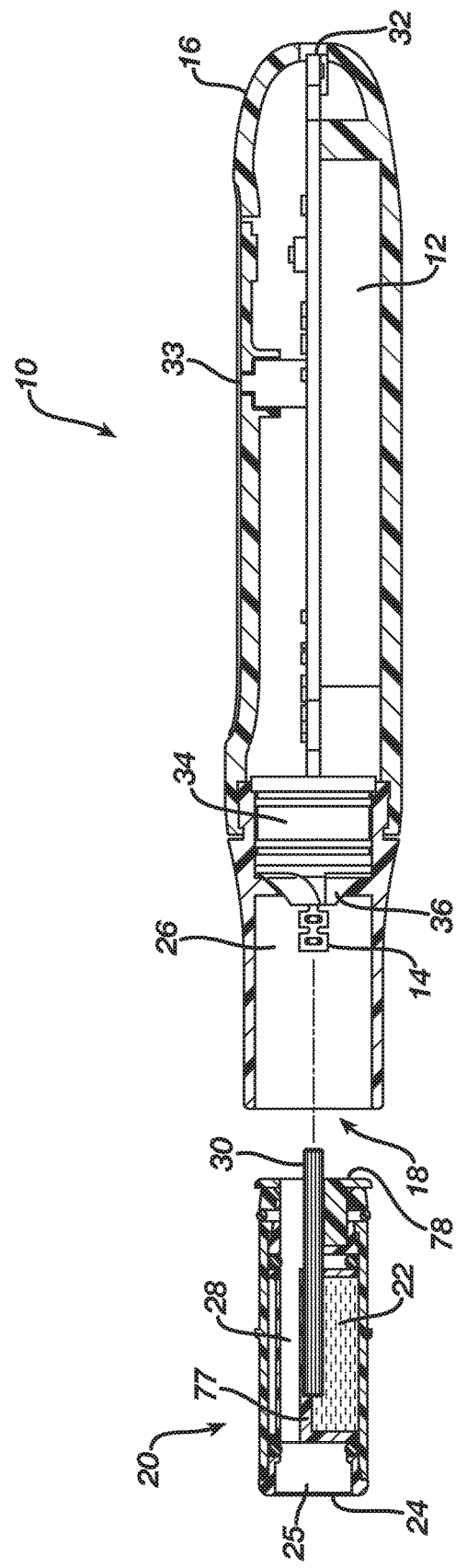
FIG. 2A is a longitudinal cross-section of the ENDS of FIG. 1 with the cartridge aligned for insertion into the housing.
Figure 2B:
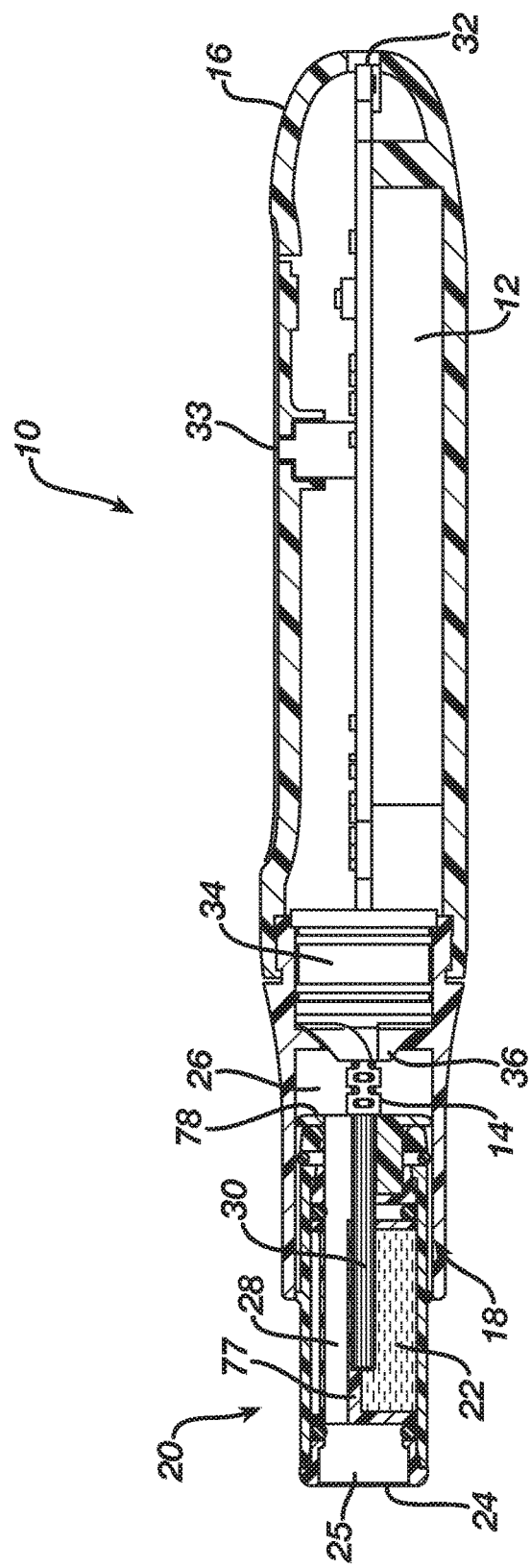
FIG. 2B is a longitudinal cross-section of the assembled ENDS of FIG. 1.
Figure 3:
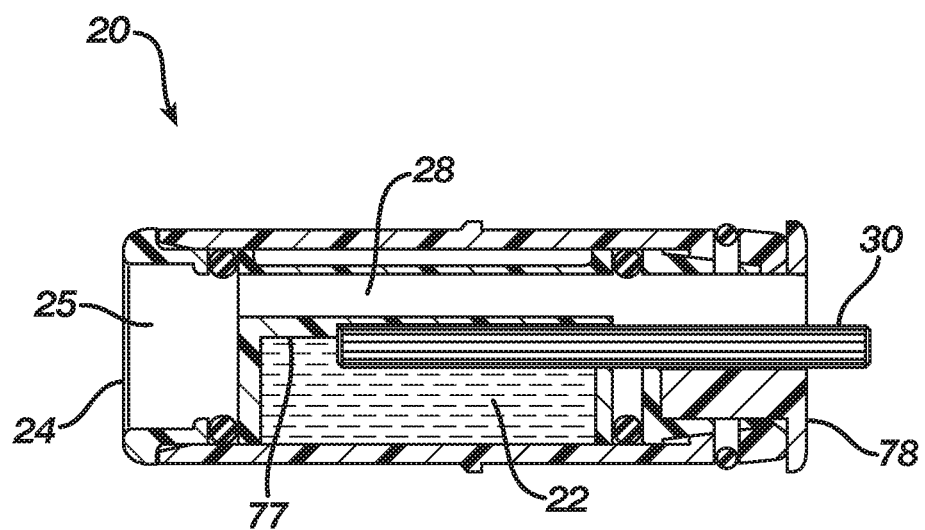
FIG. 3 is a cross-section of a disposable cartridge useful in the ENDS of FIG. 1.

Referring to FIGS. 1-3, the electronic nicotine delivery system ("ENDS") 10 includes a power source 12 and an electric heater 14 contained within a housing 16. The housing 16 has at least one air inlet 17 and provides a receptacle 18 for a disposable cartridge 20 proximate the electric heater 14. The disposable cartridge 20 preferably includes a reservoir 22 containing a nicotine solution and a mouthpiece 24 having an outlet 25 for drawing a nicotine aerosol from the ENDS 10. At least when assembled, the housing 16, electric heater 14, and cartridge 20 cooperate to form a vaporization chamber 26. The assembled ENDS 10 also provides a predetermined airflow from the at least one air inlet through the vaporization chamber 26, an outlet conduit 28 and to the outlet 25 of the mouthpiece 24 to permit a user to inhale the nicotine aerosol formed therein. In addition, the assembled ENDS 10 provides a liquid conduit from the reservoir 22 to the electric heater 14, preferably an elongate wick 30. The housing 16 may also provide for connectivity to an outside electrical source and/or data communication, such as a Universal Serial Bus ("USB") port 32, to supply and/or resupply the internal power source 12, preferably a rechargeable battery.

The internal power source 12 is sufficient to power the electric heater 14, a programmable controller (not shown), and any desired feedback to a user (e.g., light 33), external computer, or network. The programmable controller receives information from a pressure sensor 34 (detecting inhalation by a user), and, possibly, other sensors (such as temperature sensors) to control the power delivered to the electric heater 14, and controls optional over temperature sensor(s), which can terminate power to the electric heater 14 to prevent undesirable and/or dangerous thermal events. The programmable controller can provide for data collection, storage and communication to the external computer. This can be communicated through a wired or wireless connection. The internal power source 12 can be any appropriate portable power source 12.

The electric heater 14 is mounted on a base plate 36 to isolate electrical resistance heater elements from other, thermally sensitive components of the ENDS 10. The electric heater 14 comprises at least one electrical resistance heater element contained in a heat diffusing material. The diffusion of the heat through the heat diffusing material generally evens out heat profile generated by the heating element(s) to prevent the formation of localized hot spots on the electric heater 14 surface.

As indicated above, the disposable cartridge 20 preferably includes a reservoir 22 containing a nicotine solution and a mouthpiece 24 for drawing a nicotine aerosol from the ENDS 10. In addition, the assembled ENDS 10 provides a liquid conduit from the reservoir 22 to the electric heater 14. In a preferred embodiment, the liquid conduit is an elongate wick 30 extending from the reservoir 22 to the electric heater 14. The elongate wick 30 intimately contacts the electric heater 14 surface to enable the thermal energy to vaporize the nicotine solution transported thereto by the elongate wick 30. As the nicotine solution is vaporized, the elongate wick 30 transports additional nicotine solution to the electric heater 14 through capillarity.

The assembled ENDS 10 also provides a vaporization chamber 26 proximate the electric heater 14. It is in the vaporization chamber 26 that the electric heater 14 vaporizes the nicotine solution transported by the elongate wick 30 and in which the vaporized nicotine solution combines with outside air drawn in through one or more inlet ports 17 to form a nicotine aerosol. The vaporization chamber 26 also communicates with the outlet 25 of the mouthpiece 24 via at least one outlet conduit 28 in the disposable cartridge 20 to permit a user to draw the nicotine aerosol into his or her mouth.

Figure 4A:
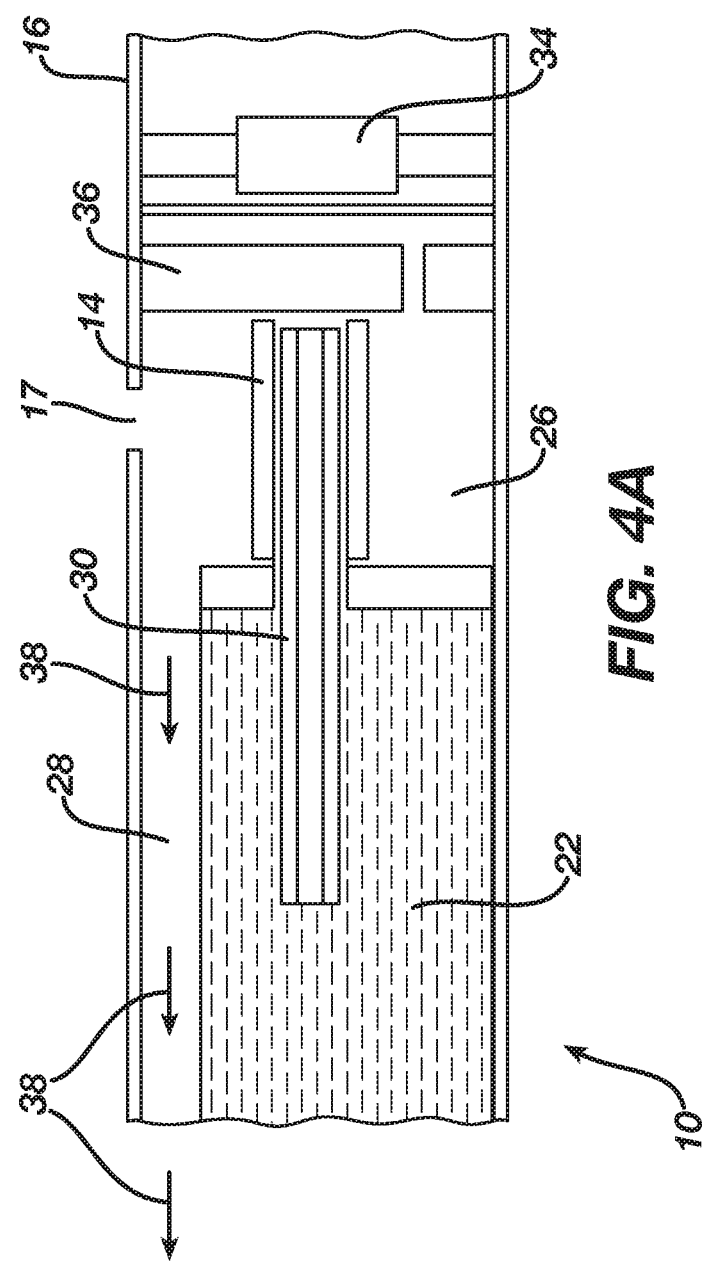
Figure 4B:
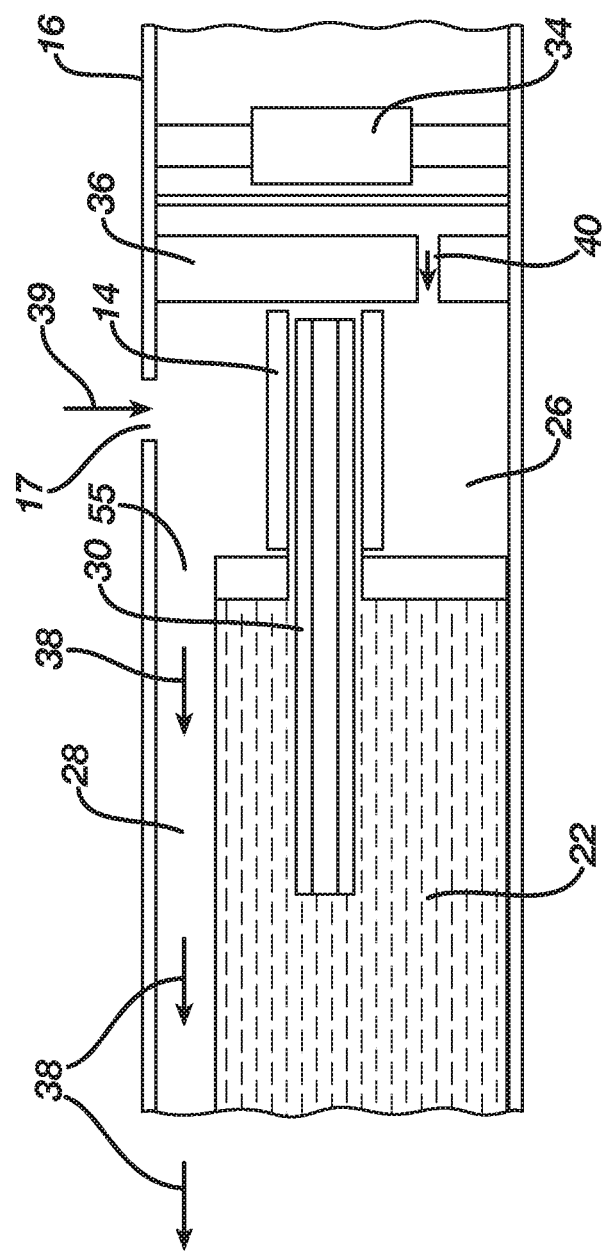
Figure 4C:
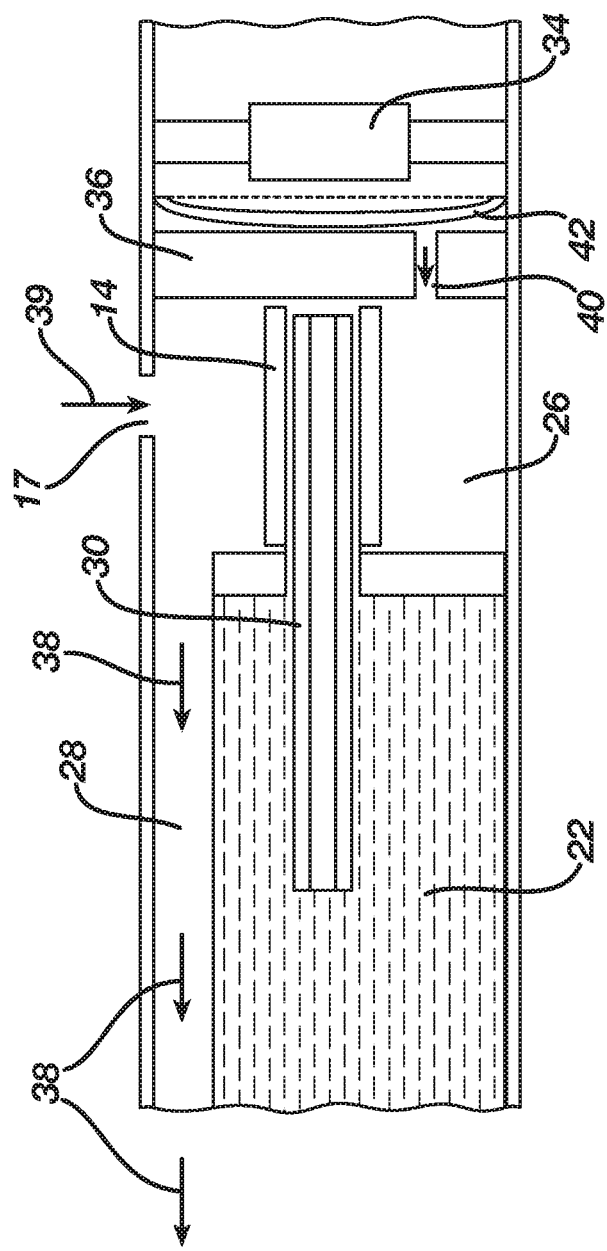
Figure 4E:
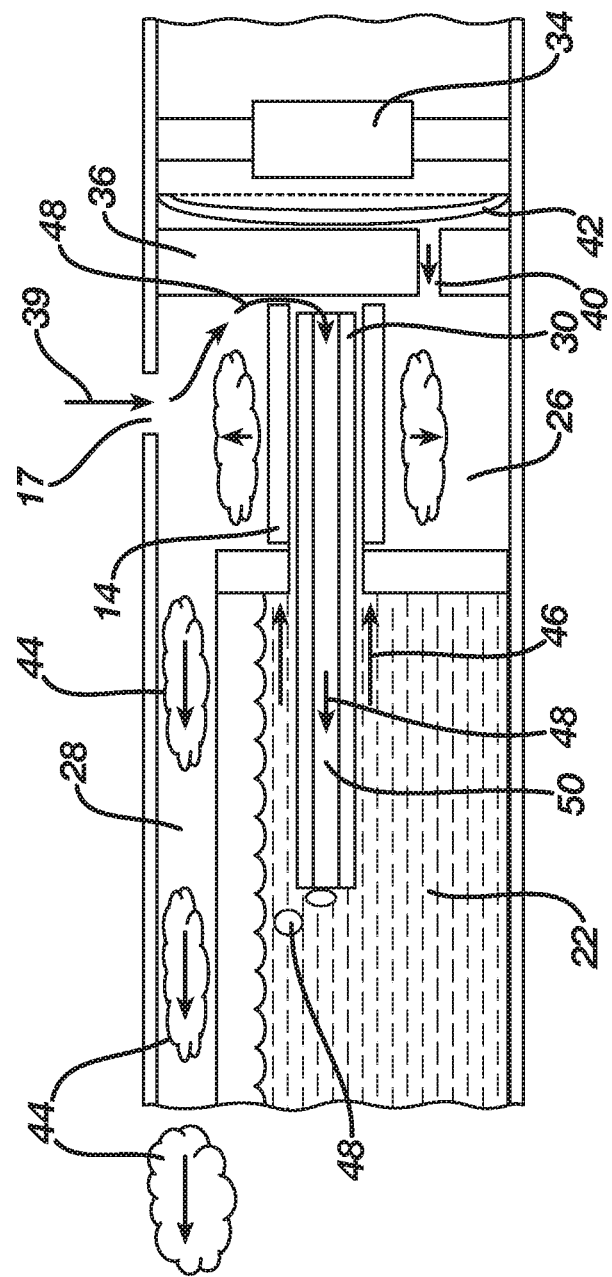
Figure 4F:
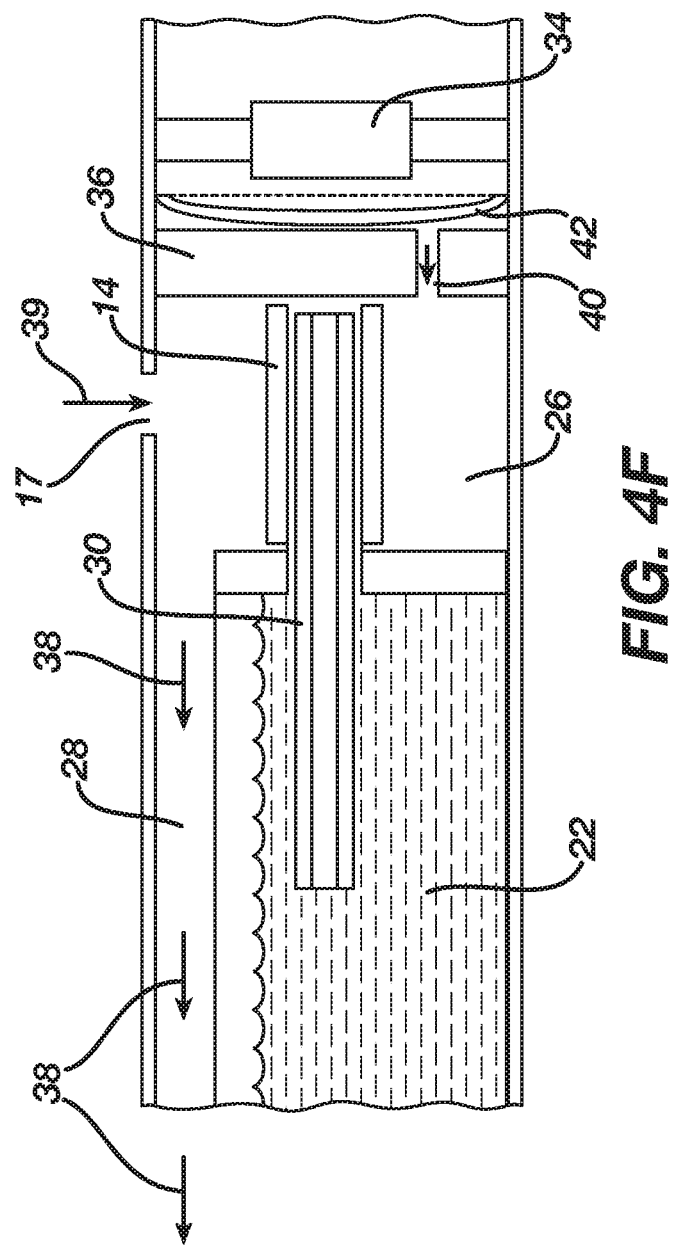
Figure 4G:
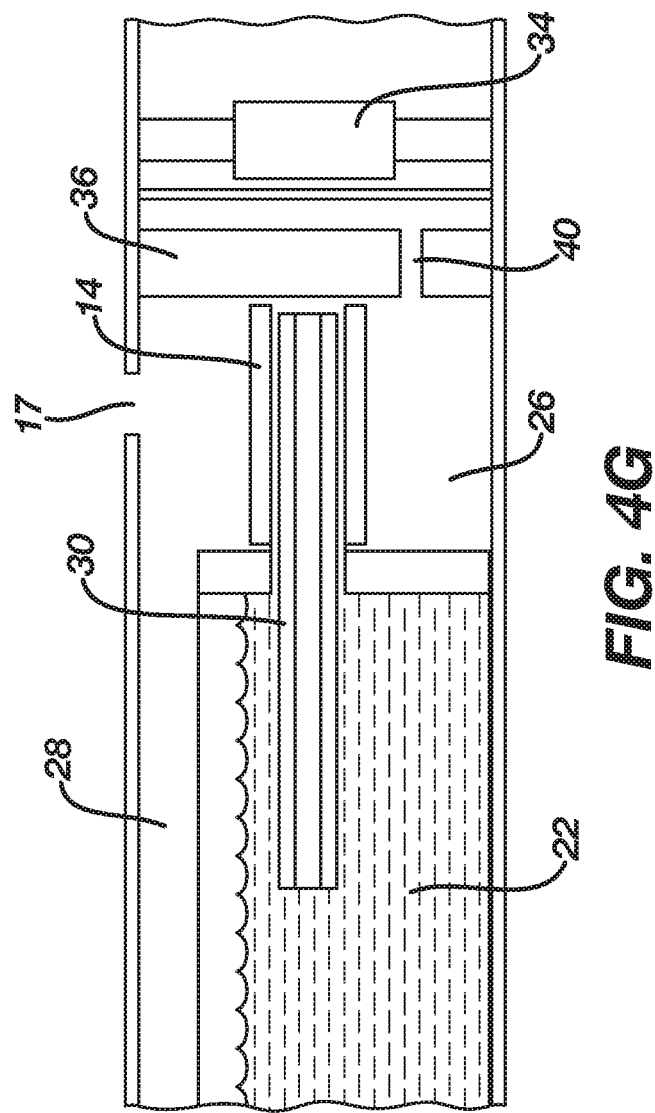

FIGS. 4A-4G illustrate one example of an air flow through the ENDS 10. These figures are schematic to explain the process and are not intended to be limiting of the actual location of all elements disclosed therein. As shown in FIG. 4A, when a user draws air from the mouthpiece, the negative pressure causes air to flow into the assembled ENDS 10. In particular, air is withdrawn from the vaporization chamber 26 through the outlet conduit 28, lowering the air pressure in the chamber 26. The withdrawn air (indicated by arrows 38) is replaced via air inlet through one or more holes 17 in the housing 16 proximate the vaporization chamber 26 (FIG. 4B). The inlet air is indicated by arrows 39. The lowered air pressure in the chamber 26 is sensed by a pressure sensor 34 disposed proximate the base plate 36, outside of the vaporization chamber 26 via a pressure equalization port 40. As shown in FIG. 4C, the equalization of pressure through pressure equalization port 40 distorts isolation membrane 42 to lower air pressure proximate the pressure sensor 34 to activate an operatively coupled switch with pressure sensor 34. This pressure sensor 34 activates the electric heater 14, which in turn heats the nicotine solution in contact therewith on the surface of the wick 30. The nicotine solution is vaporized and combined with air in the vaporization chamber 26, forming a nicotine aerosol 44 (shown in FIG. 4D). The nicotine aerosol 44 is evacuated from the vaporization chamber 26 through the outlet conduit 28 and delivered to the mouthpiece 24 and, ultimately, the user's mouth (FIG. 4D). As the nicotine solution is vaporized, additional solution is drawn from the reservoir 22 along wick 30 to electronic heater 14 as shown by nicotine solution transport arrows 46. The volume of nicotine solution removed from reservoir 22 is replaced by air 48 (indicated by arrows) drawn through the inner bore 50 of wick 30 (FIG. 4E), described in further detail, below. In one embodiment, after a predetermined time (e.g., determined by the programmable controller), the power to the electric heater 14 is terminated, the vaporization chamber 26 cools, and no further nicotine aerosol is formed (FIG. 4F). The user will then stop drawing on the ENDS 10, ending his/her "treatment" (FIG. 4G). Alternatively, the user may stop drawing on the device prior to the predetermined time. In such a case, the pressure in the vaporization chamber 26 will return to atmospheric pressure, the isolation membrane 42 will relax, and pressure sensor 34 will signal switch to terminate power to the electric heater 14.

The disposable cartridge 20 has a number of features to increase the safety of the system. In one embodiment, the disposable cartridge 20 securely locks into the housing 16 in a manner that it is not easily removed by hand; removal from the housing 16 requires interaction with a container (described in greater detail, below) for the disposable cartridge 20. In a further embodiment, the disposable cartridge 20 is not easily re-fillable with another liquid. In another embodiment, an unused disposable cartridge 20 is locked in a container until use; removal from the container requires interaction with an empty ENDS 10 housing 16. Thus, the disposable cartridge 20 is secured by either the ENDS 10 for use or a container (described in greater detail, below) for storage and/or disposal. This greatly reduces the potential for unintended exposure of the nicotine solution to the environment and/or children as this design significantly reduces the ability to access the nicotine solution contained in the disposable cartridge 20. This is substantially through use of the ENDS 10 and the conversion of the nicotine solution to an aerosol. It is difficult to otherwise access the liquid contents when the cartridge is secured in either the ENDS 10 and/or container containing the disposable cartridge 20.

The ENDS 10 can be used with accessories such as a charging case, which may include additional power supply and electronics.

Housing:

The housing 16 may comprise any suitable material or combination of materials. Preferably, it includes one or more hard, heat-resistant material(s). Examples of suitable materials include, without limitation, metals, alloys, plastics or composite materials containing one or more of those materials, or ceramics. Plastics can include thermoplastics that are suitable for food or pharmaceutical applications, for example, polypropylene, polyetheretherketone (PEEK) and polyethylene. Preferably, the material is light and non-brittle. The housing 16 may be fabricated by plastic injection molding, or any other suitable technique, and it is preferably ergonomic and adapted to fit comfortably in a hand of a user. In one embodiment, the housing 16 may have a maximum length dimension of up to about 20 cm and a maximum dimension perpendicular to the length of up to about 10 cm.

Power Source:

The internal power source 12 is sized to provide sufficient power for the electric heater 14 that vaporizes the nicotine solution and any other electronic controls included in the assembled ENDS 10. It is preferably replaceable and/or rechargeable and may include devices such as a capacitor or, more preferably, a battery. In a presently preferred embodiment, the power source 12 is a replaceable and/or rechargeable battery, although it could include a quick-discharging capacitor power source 12 that is charged by one or more battery cells. The characteristics required of the power source 12 are selected in view of the characteristics of all components in the ENDS 10. Preferred rechargeable battery cells include, without limitation, lithium-based cells, including lithium polymer batteries. One example of an internal power source 12 is a lithium polymer cell providing a voltage of about 3.4 V that has a capacity of at least about 200 milliamp hours (mAh).

The internal power source 12 is preferably in electrical communication with a coupler (such as a USB port 32) for connectivity to an outside electrical source. However, a preferred system prevents the user from using the ENDS while charging the device. This coupler can also provide for information transfer between an internal process controller and external networks and or computing devices including, without limitation, a smart charging case, smart phone, portable computing device, desktop computer, or the Internet or other local and/or wide area networks.

Electronics:

In one embodiment, as described in FIGS. 4A-4G, the pressure switch/sensor 34 in the electronic control circuit is configured to detect the drawing of air through ENDS 10, especially through the vaporization chamber 26, and an electric circuit is closed between the internal power source 12 and the electric heater 14. The process controller controls an amount of voltage/current to be delivered to the electric heater 14. The electric heater 14 outputs a sufficient amount of heat to vaporize at least a portion of the nicotine solution, which the user then draws as a nicotine aerosol 44. When the user ceases to draw air through the mouthpiece 24 and air outlet, the pressure sensor 34 detects the lack of airflow (or pressure drop) in the vaporization chamber 26, and the electric circuit between the internal power source 12 and electric heater 14 is opened (e.g., directly by the pressure sensor 34 or responsive to receipt of instructions from the process controller) with or without delay circuitry built into the control. Manual switching or activation of the power source 12 is also an option.

In one embodiment, process controller can be a microchip or controller that operates as desired when used by the user. Thus, the process controller can receive readings from the switch/sensor 34, and can cause the voltage/current to be supplied to the electric heater 14 as a function of such readings. The switch/sensor 34 can be a switch, a sensor, or a combination of a switch and sensor. For instance, the switch/sensor 34 may comprise an electronic airflow sensor, wherein the electronic airflow sensor senses when the user is drawing on the ENDS 10. Still further, the switch/sensor 34 may comprise a timed switch that opens the circuit between the internal power source 12 and the electric heater 14 after the circuit has been closed for a threshold amount of time. There are a variety of switches and sensors that can be used to detect air flow and/or pressure that can be utilized to activate the heating element.

In addition, signaling elements, such as lights (e.g., signal light 33), sounds, and/or scents can be included in and/or controlled by the electronic control circuitry.

Electric Heater:

In one embodiment, the electric heater 14 includes a base plate 36 and an electric heater 14. The base plate 36 operates as a mounting surface for the electric heater 14 and a thermal barrier between the vaporization chamber 26 and other housing 16 components, such as controllers/control circuitry and/or the internal power source 12. As shown in FIG. 5A, the base plate 36 can provide one or more air passages (e.g., pressure equalization port 40 and air inlet passage 52). The base plate 36 also provides one or more passageways for electrical conductors to connect the electric heater 14 to the internal power source 12.

Generally, any material that can be machined, or more preferably molded, to the desired shape and that can withstand chemical degradation by the liquids used in the system and high temperatures (e.g., in excess of 150° C. or even 200° C.) can be used to make the base plate. Preferred materials include, without limitation, thermoset polymers, thermoplastic polymers, and ceramics. Particularly preferred materials include ceramics and heat-resistant thermoplastic polymers. A representative, non-limiting list of useful heat-resistant thermoplastic polymers include liquid crystal polymers ("LCP"), Polyetheretherketone (PEEK), Polyether Imide (PEI), Polyphenylene Sulfide (PPS), fluorpolymers, Polyimides, Polyamideimides (PAIs), High-performance polyamides (HPPAs), Polyimides (PIs), Polyketones, Polysulfone derivatives, Polycyclohexane dimethyl-terephthalates (PCTs), Fluoropolymers, Polyetherimides (PEIs), Polybenzimidazoles (PBIs), Polybutylene terephthalates (PBTs), Syndiotactic polystyrene, Acrylonitrile-Methyl acrylate copolymers (for example Barex® resins Velox, Hamburg, Germany), and the like.

The electric heater 14 includes electrical resistance heater elements substantially encapsulated within a substantially non-porous ceramic material, the heat diffusing material. The non-porous nature of the ceramic material encapsulating the heater elements substantially eliminates direct contact between the nicotine solution and the resistance heater elements. This minimizes the formation of localized hot spots on the electric heater 14 surface that contact the nicotine solution. This reduces the likelihood of overheating of both the components of the nicotine solution and the elongate wick 30. Indeed, this permits the use of wicks that cannot operate directly contact with metallic, resistance heating elements, such as tungsten and/or copper wire. Many commercial devices employ bundles of glass fibers as wicks, and these wicks are wrapped with bare metal wires. Examples described in patent literature include Philip Morris Products, S.A., Eur. Pat. App. Pub. No. EP2 606 756 A1; and Tucker et al., US Pat. App. Pub. No. US2013/0192615 A1. In contrast, the present invention permits the use of a polymeric wick, even an extruded wick formed of substantially non-porous, durable, thermoplastic material, as described below.

In one preferred embodiment, the electric heater 14 includes resistance heater elements formed of electrically resistive materials encapsulated in a substantially non-porous ceramic material. The electrically resistive materials may be in the form of a wire, flakes, foil or film, a continuous or patterned coating, and the like deposited (e.g., printed, sprayed, coated, and the like) or formed on a ceramic material that is further processed to encapsulate (and fuse, as appropriately) the electrically resistive material in the ceramic material.

Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminum-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® titanium alloy, and iron-manganese-aluminum based alloys.

In one embodiment, the electrically resistive material may take the form of a metallic etched foil (or film) encapsulated between two layers of an inert, heat diffusing material. In that case, the inert material may comprise Kapton® polyimide or mica foil. The etched foil may comprise a metal sheet cut by a laser or by electro-chemical process and formed into a desired pattern. The sheet may be rectangular in shape, or may have a patterned shape which may form a coil-like structure when rolled around the capillary wick 30. Other alternatives include a heating wire or filament, for example a Ni—Cr, platinum, tungsten or alloy wire embedded in the ceramic material.

Figure 6A:
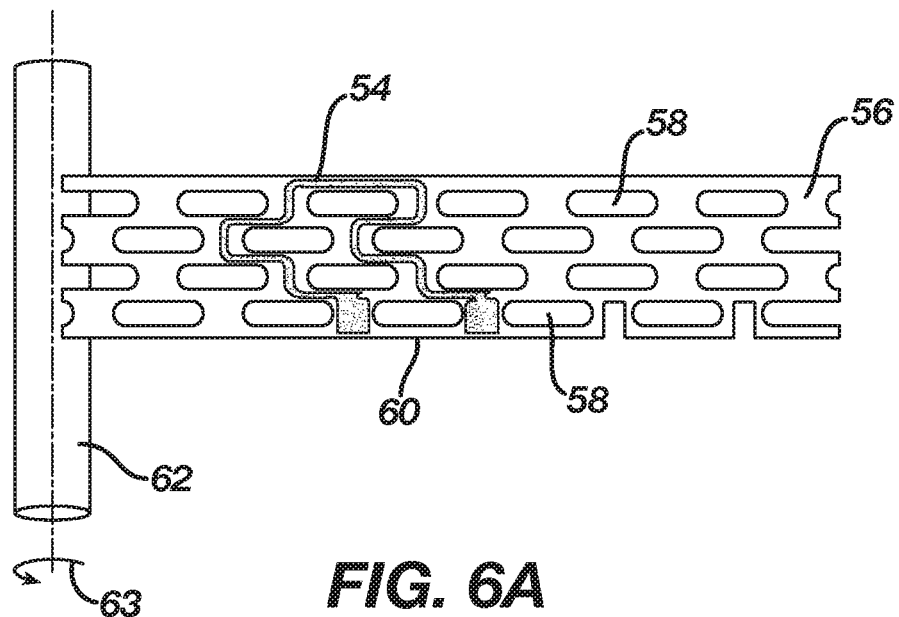
FIG. 6A is a schematic view of a green ceramic substrate useful in the formation of an electric heater of the present invention.
Figure 6B:
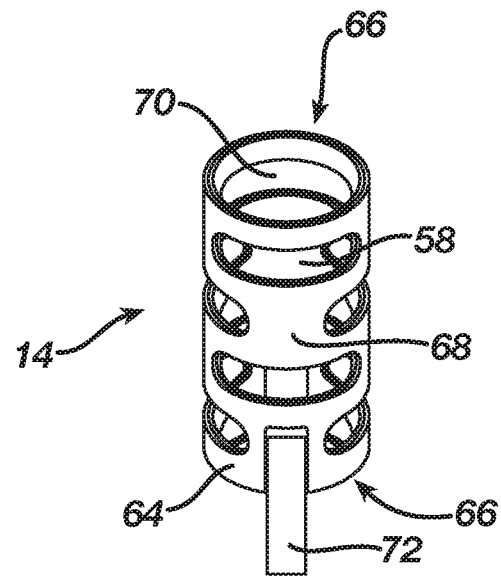
FIG. 6B is a perspective view of a multilayered green ceramic heater element formed from the substrate of FIG. 6A.

In one preferred embodiment shown in FIGS. 6A-B, the electric heater 14 employs tungsten-doped material as the electrically resistive material 54 formed on a green (unfired) ceramic substrate 56. Preferably, the material is printed or coated onto the green ceramic substrate. A preferred green ceramic substrate 56 is formed having a pattern of macro apertures 58 formed therein. A trace of the electrically resistive material 54 is deposited in a continuous path on a portion of a green ceramic substrate 56, beginning and ending at one edge 60 of the green ceramic substrate 56. The green ceramic substrate 56 is then wrapped about a cylindrical mandrel 62 (in the direction indicated by arrow 63) to form a green ceramic heater element 64 with open ends 66 formed of three layers of the green ceramic substrate 56, each layer superposed on a preceding layer with the apertures 58 substantially indexed to provide continuous macro apertures from the outer surface 68 of the green ceramic heater element 64 to its resulting inner bore 70. The electrically resistive material 54 is encapsulated within the layers of the green ceramic heater element 64, and two electrical tabs 72 are provided in electrical contact with the ends of the electrically resistive material 54. These tabs are then available for electrical connection through the base plate 36, as described above. The green ceramic heater element 64 is then fired (heated to very high temperature to fuse the ceramic material) to form the electric heater 14, as will be recognized by those of ordinary skill in the art.

In an alternative embodiment, the macro apertures 58 may be formed after the green ceramic substrate 56 is wrapped about the mandrel 62.

More generally, the electric heater has a body formed of at least one sidewall that defines a length, an interior void, at least one inner surface (e.g., the inner bore 70), at least one outer surface (e.g., the outer surface 68), and a plurality of apertures 58 through the at least one sidewall and/or between adjacent sidewalls connecting the inner surface 70 and the outer surface 68. Thus, the nicotine vapor can to escape the heater/wick combination from the inner bore 70 through the macro apertures 58 into the volume of the vaporization chamber 26.

The electric heater can take many shapes that provide inwardly- and outwardly-directed surfaces. For example, a simple tubular structure has been described. Other tubular structure can include those with circular, elliptical polygonal and other closed cross-sections. Alternative forms of the heater can be include channel heaters that have an open wall to provide a cross-section of a "c-shape", a "u-shape", a "v-shape", or other open, channel structures. Alternatively, the body may be formed of a plurality of fingers, each providing a sidewall, and the sidewalls collectively define the interior void.

In addition, the maximum dimension perpendicular to the electric heater length (e.g., a diameter of a tubular electric heater) can vary to provide a conical or frusto-conical shape or other socket-like shapes to accept or to hold a wick in intimate contact with the inwardly-directed surface.

Cartridge:

As indicated above, the housing 16 provides a receptacle 18 for the disposable cartridge 20 proximate the electric heater 14, and the disposable cartridge 20 includes a reservoir 22 containing a nicotine solution. While the following description references a nicotine solution, other, vapor-forming solutions can be employed in the device of the present invention.

Generally, nicotine solutions include at least a combination of water, propylene glycol and/or glycerin, and nicotine. In some cases, solutions may include from about 2 to about 10 wt-% nicotine, from about 0 to about 30 wt-% water, from about 65 to about 95 wt-% propylene glycol and/or a mixture of propylene glycol and glycerin. These solutions have a boiling point of between about 105° C. and about 150° C., a viscosity of between about 10,000 and about 60,000 mPas (milli-pascals). In one embodiment, a nicotine solution includes at least 12 percent by weight of water, at least 70 percent by weight of propylene glycol; and at least 2 percent by weight of nicotine or a salt thereof. In one embodiment, the liquid formulation contains at least 15 percent by weight of water, such as at least 20 percent by weight of water. In one embodiment, the liquid formulation contains at least 75 percent by weight of propylene glycol, such as at least 80 percent by weight of propylene glycol, such as at least 85 percent by weight of propylene glycol.

Figure 7:
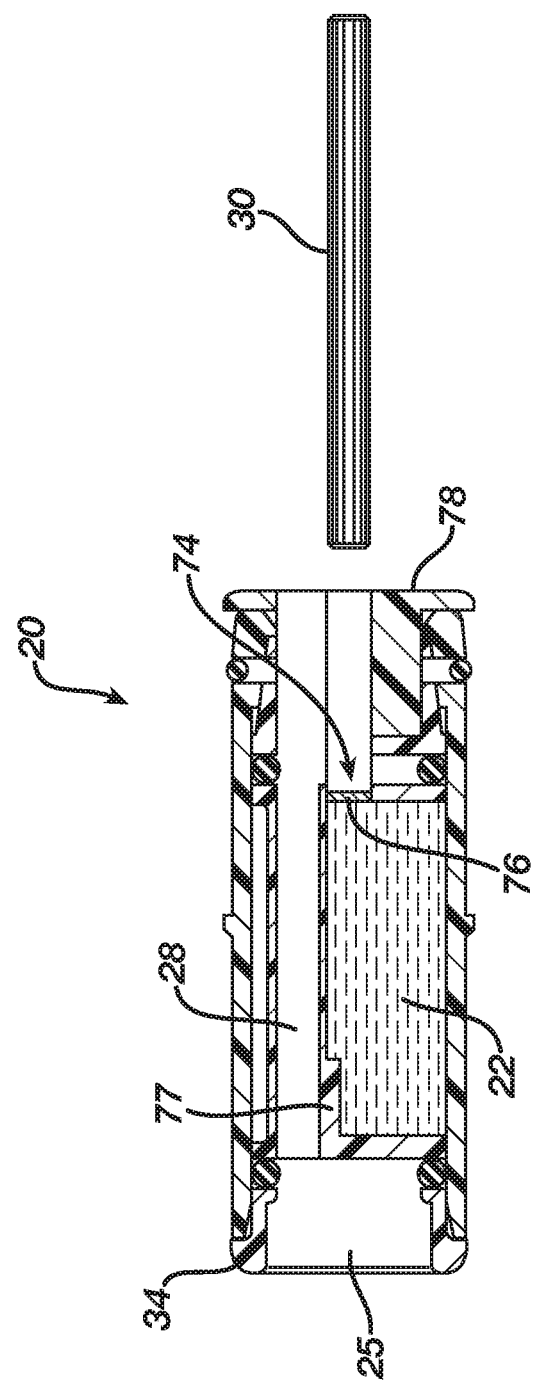
FIG. 7 is a cross-section of the disposable cartridge of FIG. 3 prior to the insertion of an elongate wick into the reservoir.

As shown in FIG. 7, the reservoir 22 includes at least one port 74 from which the nicotine solution can be withdrawn and directed to the vaporization chamber 26 in the assembled ENDS 10. However, prior to use, a liquid barrier or seal, such as a barrier membrane 76 is disposed to prevent leakage of the solution through the port 74. In embodiments in which the elongate wick 30 is incorporated into the disposable cartridge 20, the elongate wick 30 can be stored, such as slidably fitted in the port 74, adjacent the barrier membrane 76, and during the locking of the disposable cartridge 20 into the receptacle 18, the elongate wick 30 can slide further into the reservoir 22 to rupture the barrier membrane 76 to provide the liquid conduit from the reservoir 22 to the electric heater 14. The penetration of the wick 30 into the reservoir 22 can be limited by means of a stop 77 (shown in FIGS. 3 and 7). In an alternative embodiment (not shown), the liquid barrier may be a seal or plug disposed about the distal end of the wick that is disposed in the port 74. In embodiments in which the elongate wick 30 extends from the electric heater 14, wick 30 would slide into the port 74 and rupture the barrier membrane 76 or break a seal at or proximate the port 74 during the locking of the disposable cartridge 20 into the receptacle 18. In alternative embodiments in which the wick is a part of replacement kit for the ENDS, the wick can be packaged with a disposable cartridge and inserted into the port 74 prior to securing the disposable cartridge to the receptacle of the housing.

As the nicotine solution is withdrawn from the reservoir 22, an equal volume of air is admitted into the reservoir 22. This replacement air may be provided through one or more vents (such as inner bore 50 of wick 30) or other reservoir vent technology known to those of ordinary skill in the art.

The disposable cartridge 20 also includes at least one air passage (outlet conduit 28) between the vaporization chamber 26 and the mouthpiece 24 to permit a user to draw the nicotine aerosol into his or her mouth. The outlet conduit 28 may have a substantially constant cross-section, or the cross-section may vary along its length. In one preferred configuration, the cross-sectional area of the outlet conduit 28 decreases away from the vaporization chamber 26. The mouthpiece 24 is preferably disposed at a portion of the disposable cartridge 20 distal to the vaporization chamber 26.

Figure 8:
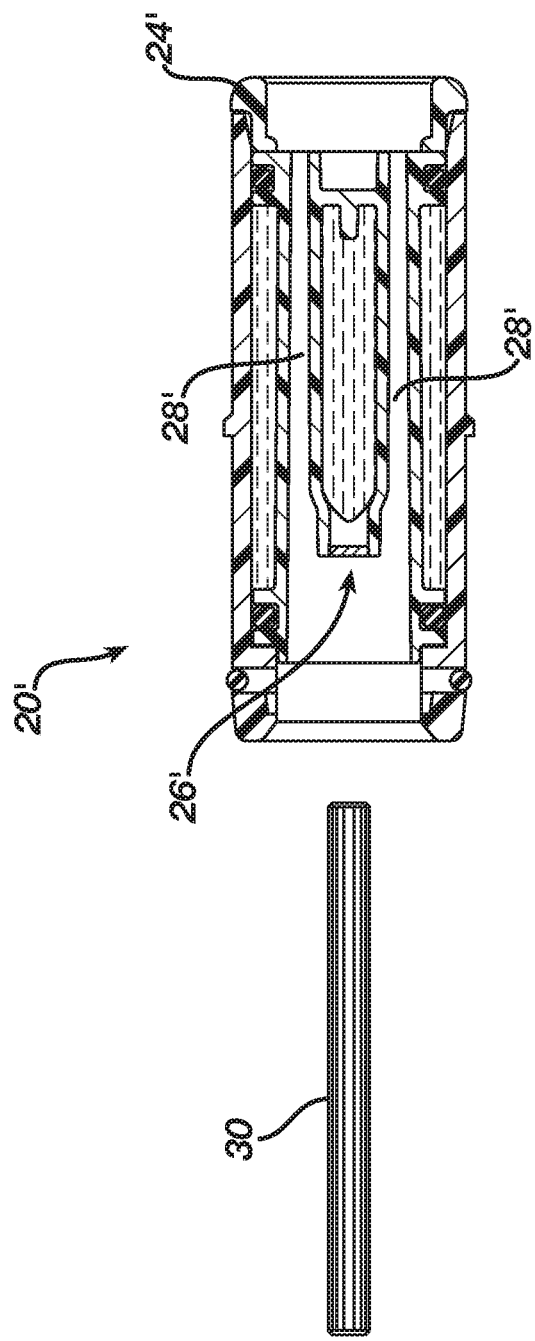
FIG. 8 is a cross-section of alternate embodiment of the disposable cartridge similar to that of FIG. 3 prior to the insertion of an elongate wick into the reservoir.
Figure 9:
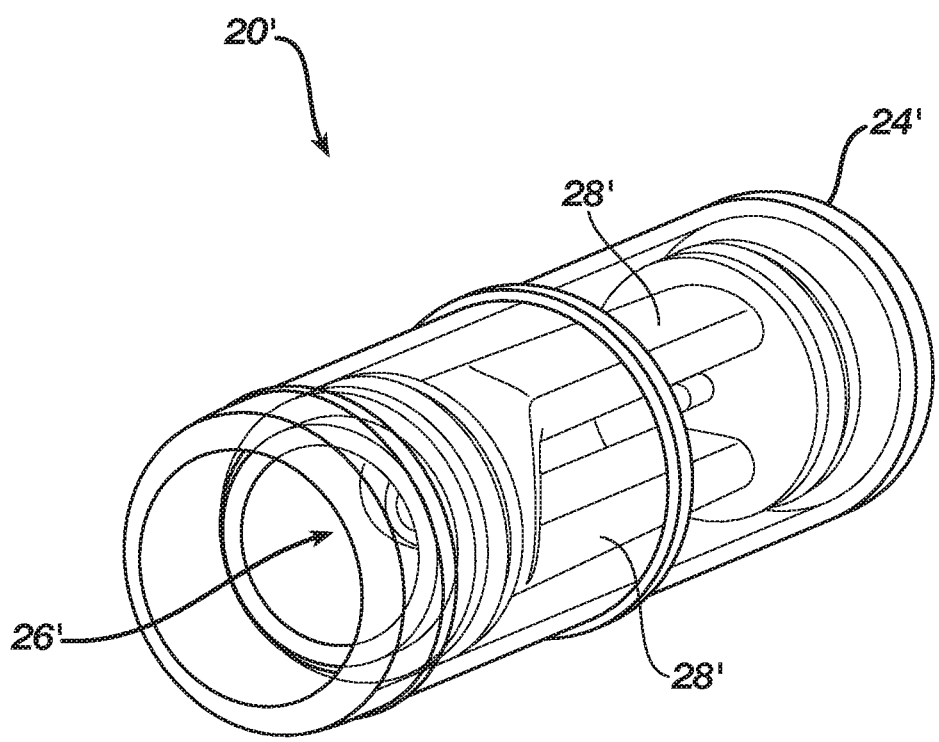
FIG. 9 is a perspective view of the disposable cartridge of FIG. 8.

While the embodiment of FIGS. 1-7 is effective, one of ordinary skill in the art will recognize that more symmetry of airflow around the heater can improve particle size distribution and reduce the likelihood of condensation in the vaporization chamber. Thus, more than one outlet conduits may be employed or the outlet conduit may be in the form of an annulus. Preferably, there are at least two outlet conduits (as shown in FIGS. 8 and 9), the disposable cartridge 20' includes two air passages (outlet conduits 28') between the vaporization chamber 26' and the mouthpiece 24' to permit a user to draw the nicotine aerosol into his or her mouth. Again, the two outlet conduits 28' may have a substantially constant cross-section, or the cross-section may vary along their length. As above, the cross-sectional area of the outlet conduits 28' may decrease away from the vaporization chamber 26'. The mouthpiece 24' is preferably disposed at a portion of the disposable cartridge 20' distal to the vaporization chamber 26'. In summary, the disposable cartridge includes at least one outlet conduit (outlet conduit 28 in FIGS. 3 and 7). More preferably, the disposable cartridge may incorporate two (outlet conduits 28' in FIGS. 8 and 9). Even more preferably, the disposable cartridge incorporates 2 to 8 outlet conduits to improve the symmetry of air flow through and out of the vaporization chamber.

In addition, as shown in FIGS. 8 and 9, the outlet conduits 28' may have a decreasing cross-section towards the mouthpiece. While not intending to be held to this theory, it is believed that a tapered outlet conduit may provide increase velocity as the aerosol is drawn from the ENDS. This increased velocity may reduce the likelihood of condensation being deposited in the cartridge or mouthpiece. The tapered outlet conduit may also provide compression to maintain the temperature of the aerosol to minimize condensation.

In one embodiment, the disposable cartridge 20 has a number of features to increase the safety of the system. As will be described in greater detail below, embodiments of the disposable cartridge 20 incorporates features to enable it to securely lock into the receptacle 18 of the housing 16 in a manner that it removable by hand without damage to the disposable cartridge 20, the housing 16, or preferably both. In addition, the disposable cartridge 20 incorporates features to enable it to securely lock into a container prior to use and after use, for disposal.

While the cartridge has been described in the context of a nicotine delivery system, alternative active ingredients may be employed in this system, such as drugs to treat asthma, pain, and other inhalably-treated conditions.

Vaporization Chamber:

The vaporization chamber 26 is defined by elements of the disposable cartridge 20, the housing 16, and the electric heater 14. In particular, the electric heater 14 is functionally at the center of the vaporization chamber 26. It is at the interface between the electric heater 14 and the nicotine solution that a nicotine-containing vapor is formed and admixed with air to form a nicotine aerosol. In the embodiment shown in FIG. 2, the base plate 36 forms one wall of the vaporization chamber 26, and an end 78 of the disposable cartridge 20 forms an opposite wall of the vaporization chamber 26. The remaining walls of the vaporization chamber 26 are formed by the housing 16. At least one, and preferably a plurality of holes 17 are formed in the housing 16 proximate the vaporization chamber 26. In a preferred embodiment shown in FIG. 5, the air holes 17 communicate, via manifold (shown as annular passage 80), with air inlet passages 52 in the base plate 36 that are angled from the longitudinal axis of the vaporization chamber 26 to create a circular air flow or vortex (illustrated by arrows 81 in FIG. 5B) about the electric heater 14 in the vaporization chamber 26. These air inlet passages 52 provide a plurality of vaporization chamber air inlet openings 53. It is believed that this improves mixing of the nicotine vapor and inlet air to form a more uniform nicotine aerosol that can be drawn through the vaporization chamber air outlet conduit 28 and to the mouthpiece 24.

While the above description refers to providing a vortex flow about the heater, one of ordinary skill in the art will recognize that alternative air flows are possible and may be selected for different desired attributes.

Generally, any material that can be machined, or more preferably molded, to the desired shape and that can withstand chemical degradation by the liquids used in the system and high temperatures can be used to make components of the vaporization chamber. Preferred materials include, without limitation, thermoset polymers, thermoplastic polymers, and ceramics. Particularly preferred materials include ceramics and heat-resistant thermoplastic polymers. A representative, non-limiting list of useful heat-resistant thermoplastic polymers include liquid crystal polymers ("LCP"), Polyetheretherketone (PEEK), Polyether Imide (PEI), Polyphenylene Sulfide (PPS), fluorpolymers, Polyimides, Polyamideimides (PAIs), High-performance polyamides (HPPAs), Polyimides (PIs), Polyketones, Polysulfone derivatives, Polycyclohexane dimethyl-terephthalates (PCTs), Fluoropolymers, Polyetherimides (PEIs), Polybenzimidazoles (PBIs), Polybutylene terephthalates (PBTs), Syndiotactic polystyrene, Acrylonitrile-Methyl acrylate copolymers (for example Barex® resins Velox, Hamburg, Germany), and the like.

Wick:

In addition, the assembled ENDS 10 provides a liquid conduit from the reservoir 22 to the electric heater 14. In a preferred embodiment, the liquid conduit is an elongate wick 30 extending from the reservoir 22 to the electric heater 14. The elongate wick 30 intimately contacts the electric heater 14 surface to enable the thermal energy provided by the electrical resistance heater elements to vaporize the nicotine solution transported thereto by the elongate wick 30. As the nicotine solution is vaporized, the elongate wick 30 transports additional nicotine solution to the electric heater 14 through capillarity.

In one preferred embodiment shown in FIG. 3, the elongate wick 30 is a component of the disposable cartridge 20, and it is formed of substantially non-porous durable thermoplastic material. This wick 30 structure is capable of being inserted into the inner bore 70 of an open, cylindrical electric heater 14 to create an intimate contact between the outer surfaces of the elongate wick 30 and the inner surfaces of the electric heater 14. Thus, the elongate wick 30 of the present invention is sufficiently rigid and robust to resist damage and significant distortion while moving axially with respect to the inner surfaces of and electric heater and/or with respect to the port of the disposable cartridge. Such a wick is preferred over wicks formed of bundles of glass fibers currently used in many electronic nicotine devices, as such fibers are likely to be broken off in the interference fit with the cylindrical heater element. The broken fiber fragments would be free to become entrained in the air stream and then possibly into a user's lungs.

An example of this preferred wick structure is shown in FIGS. 8A-C as a tubular durable thermoplastic material having a plurality of liquid-conducting features, such as longitudinally extending ribs 82 projecting from the outer surface thereof. This provides capillary channels between the ribs 82 to conduct the nicotine solution along the outer surface of the elongate wick 30 from the reservoir 22 to the cylindrical electric heater 14. In one embodiment, the dimensions of the inner bore 50 of the elongate wick 30 are selected to discourage capillary transport of the nicotine solution through the inner bore 50 and to permit air to be drawn into the reservoir 22 to equalize pressure as nicotine solution is removed therefrom (as shown in FIG. 4E). Such an elongate wick 30 can be formed by extruding the plastic through one or more dies. One preferred form of extrusion includes extruding the central tube and co-extruding the ribs 82 onto the surface of the tube.

The material selected for the wick can be any material that can be formed to be sufficiently rigid to withstand the forces involved in slidably engaging other components of the ENDS, including the electric heater 14, the disposable cartridge port 74. It also should be resistant to thermal degradation up to a temperature of at least about 180° C. Preferably, the material is resistant to thermal degradation up to a temperature of at least about 200° C., and more preferably, at least about 250° C.

Generally, any material that can be machined, or more preferably molded, to the desired shape and that can withstand chemical degradation by the liquids used in the system and the high temperatures discussed above can be used to make the wick, and it is preferred that the materials have low thermal conductivity to avoid overheating liquid in the reservoir 22. Preferred materials for the elongate wick include thermoset polymers, thermoplastic polymers, and ceramics. Particularly preferred materials include ceramics and heat-resistant thermoplastic polymers. A representative, non-limiting list of useful heat-resistant thermoplastic polymers include liquid crystal polymers ("LCP"), Polyetheretherketone (PEEK), Polyether Imide (PEI), Polyphenylene Sulfide (PPS), fluoropolymers, Polyimides, Polyamideimides (PAIs), High-performance polyamides (HPPAs), Polyimides (PIs), Polyketones, Polysulfone derivatives, Polycyclohexane dimethyl-terephthalates (PCTs), Fluoropolymers, Polyetherimides (PEIs), Polybenzimidazoles (PBIs), Polybutylene terephthalates (PBTs), Syndiotactic polystyrene, and the like. Preferred materials include PEEK, PEI, LCP (for example Vectra® liquid crystal polymers available from Celanese), and the like.

Figure 10A:
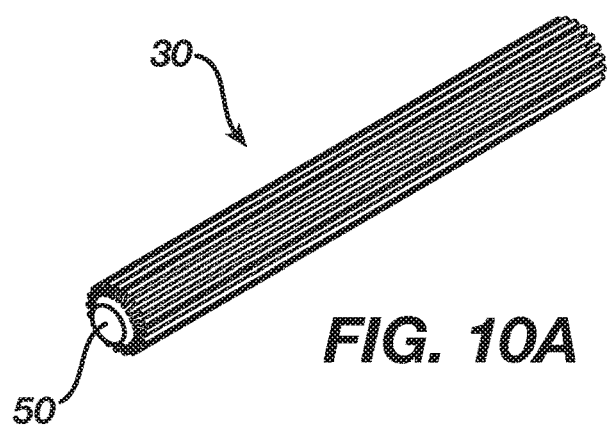
FIG. 10A is a perspective view of an elongate wick useful in the practice of the present invention.
Figure 10B:
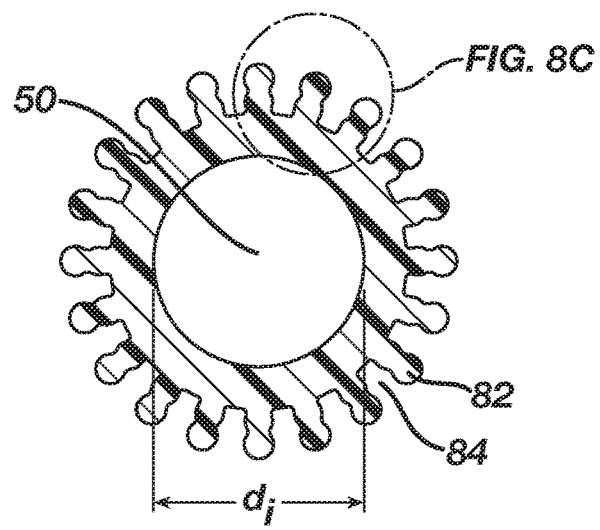
FIG. 10B is a cross-section of the elongate wick of FIG. 10A.
Figure 10C:
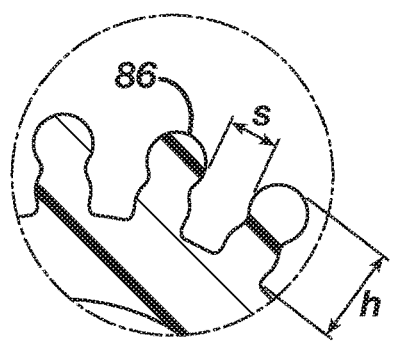
FIG. 10C is an enlargement of a portion of the cross-section of FIG. 10B.

As can be seen from FIG. 10B, the diameter "di" of the inner bore 50 is much greater than the spacing "s" between adjacent ribs 82 on the outer surface of the elongate wick 30. The spacing "s" and height "h" of the ribs 82 is selected to effectively transport the nicotine solution in the channels 84 formed between adjacent ribs. The height "h" is measured from the base of the channel 84 between ribs and the outermost tip of the rib. The spacing "s" is measured between adjacent ribs at 90% of their height. It will also be recognized that the transport properties of the channels 84 can be modified, as desired, by appropriate surface treatment (including coatings) to improve the wettability of the surfaces of the channel by the nicotine solution. The height "h" of the ribs is also determined by the effectiveness of heat transfer from the inner bore 70 of the electric heater 14 to the nicotine solution transported by the channels 84, as the inner bore 70 of the electric heater 14 will be in contact with or at least in close proximity to the outer ends 86 of the ribs 82 during use. While the surface of the heater elements and the liquid surface do not have to be in contact, we have found that the system tolerates a gap between the outer ends of the ribs and the heater element. Preferably, the gap is less than about 0.3 mm, and more preferably, the gap is less than about 0.2 mm. It is believed that the gap between the heater element and the nicotine solution is quickly filled with saturated vapors and such a gap can therefore conduct heat from the heater surface to the liquid better than a dry air gap.

As indicated above, the inner bore 50 of the elongate wick 30 serves to permit air ingress into the reservoir 22 to equalize pressure as nicotine solution is removed. Unfortunately, under some conditions, the inner bore 50 may also provide a potential pathway for leakage of the nicotine solution therethrough, so the surface of the inner bore 50 may be treated (either by coating or physical surface treatments) to reduce its wettability by the nicotine solution. Alternatively, a check valve (not shown) may be used to permit air ingress through the bore 50 and prevent undesired nicotine solution leakage. In one embodiment, the surfaces of the heater 14 that contact the wick 30 are designed to minimize wettability by the nicotine solution in order to reduce the likelihood of nicotine solution leakage via capillarity along the channels 84 when the heater 14 is not activated, e.g., by applying a coating that is not easily wetted by the nicotine solution.

In yet another alternative embodiment, the central bore 50 may be plugged to prevent leakage of the nicotine solution and an alternative reservoir vent system may be used.

Figure 11:
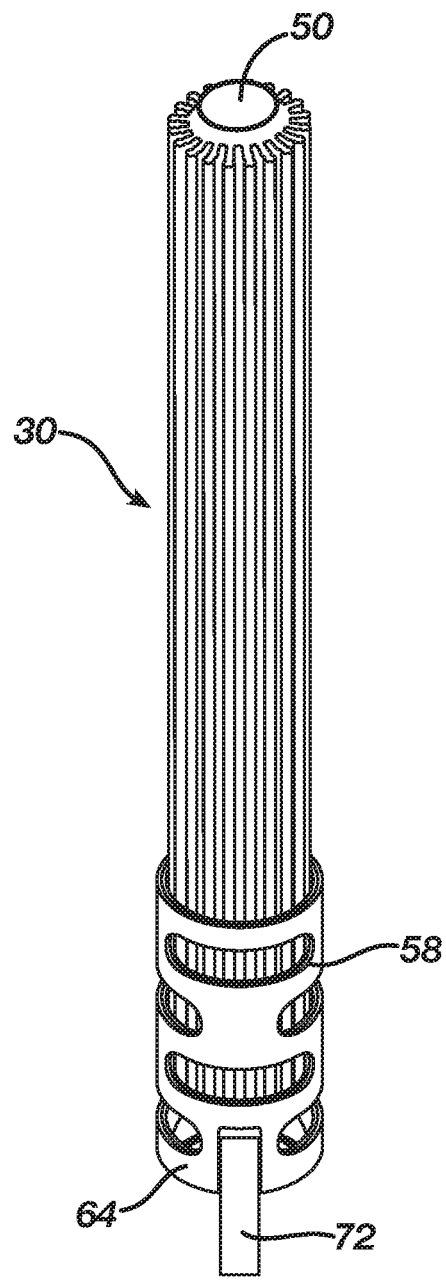
FIG. 11 is a perspective view of a multilayered green ceramic heater element formed about a ceramic wick mandrel.

In an alternative embodiment, the elongate wick 30 is associated with the electric heater 14. In this embodiment, the elongate wick 30' may be a ceramic material formed with the electronic heater. Indeed, a fired ceramic wick 30' may be used in place of the forming mandrel 62 (FIG. 6A) and the green ceramic material may be wrapped around the elongate wick 30'. The resulting combination of wick 30' and cylindrical electric heater 14' can be fired together to form an integrated wick/heater structure shown in FIG. 11. In this embodiment, a distal end of the elongate wick 30' extends significantly beyond an end of the cylindrical electric heater 14' to enable it to extend into the reservoir 22 in the disposable cartridge 20 (FIG. 7).

In another alternative embodiment, the elongate wick 30 has substantially non-porous support and a capillary structure on an outer surface thereof. The non-porous support may be solid or tubular in structure, depending whether it is desirable to permit air to vent back into the reservoir.

Container:

The container 88 is useful to provide critical child-resistant safety measures to the disposable cartridge(s) 20. In particular, the container 88 locks an unused disposable cartridge(s) 20 securely in a package. In addition, the container 88 includes empty "waste" chamber(s) sized to contain a used disposable cartridge 20. The container 88, disposable cartridge 20, and receptacle 18 in the housing 16 all cooperate to securely lock the cartridge 20 into either the receptacle 18 or the container 88. This greatly reduces the potential for unintended exposure of an unattached disposable cartridge 20 that contains the nicotine solution to the environment and/or children. It is desired that the access to the nicotine solution contained in the disposable cartridge 20 is through use of the ENDS 10 and the conversion of the nicotine solution to an aerosol. Other access to the liquid contents are difficult, at best, such as through the destruction of the ENDS 10 and/or container 88 containing the disposable cartridge 20.

Figure 12D:
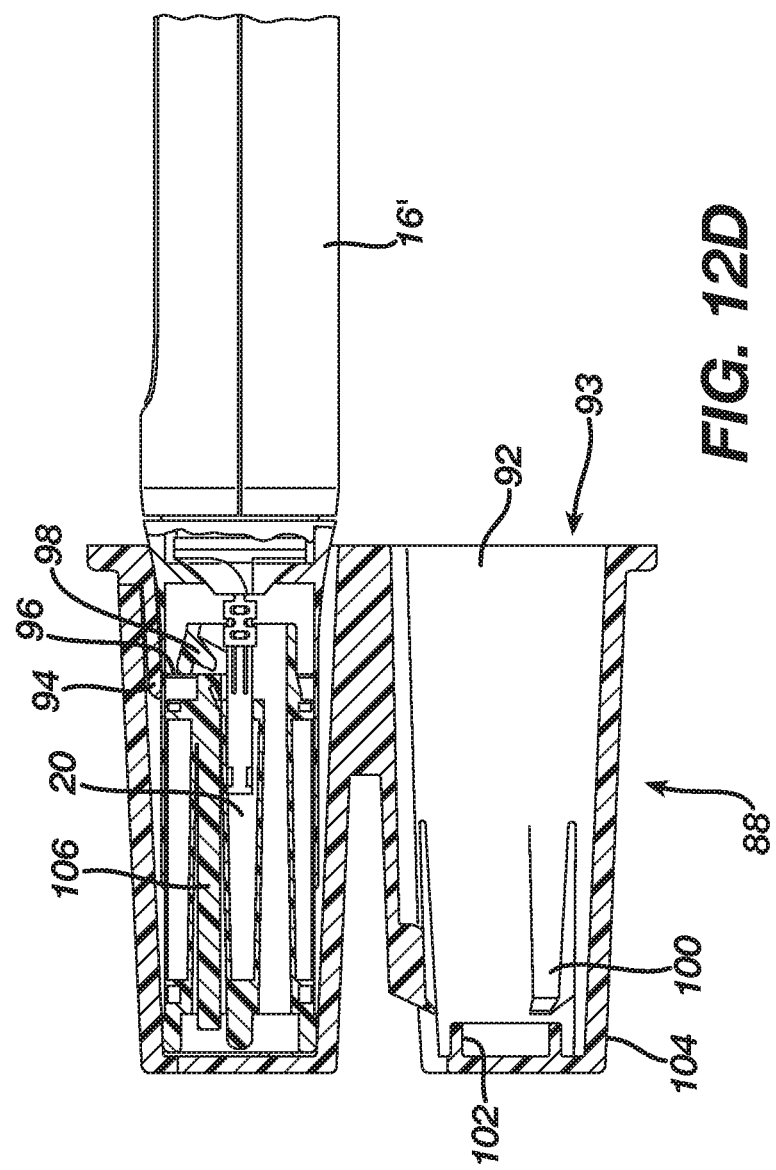

As shown in FIG. 12A, a modified ENDS 10' having an extended receptacle sleeve 18' can be used with the particular embodiment of a container described below. The steps required to remove an unused disposable cartridge are shown in FIGS. 12B-E.

The container 88 includes at least one first chamber 90 having an opening 91 sized to contain an unused disposable cartridge 20 and at least one waste chamber 92 having an opening 93 sized to contain a used disposable cartridge 20. Each unused disposable cartridge 20 is maintained in a first chamber 90 by a first, releasable engagement mechanism, and each waste chamber 92 has a second engagement mechanism to secure such used disposable cartridge 20, after use.

Figure 12E:
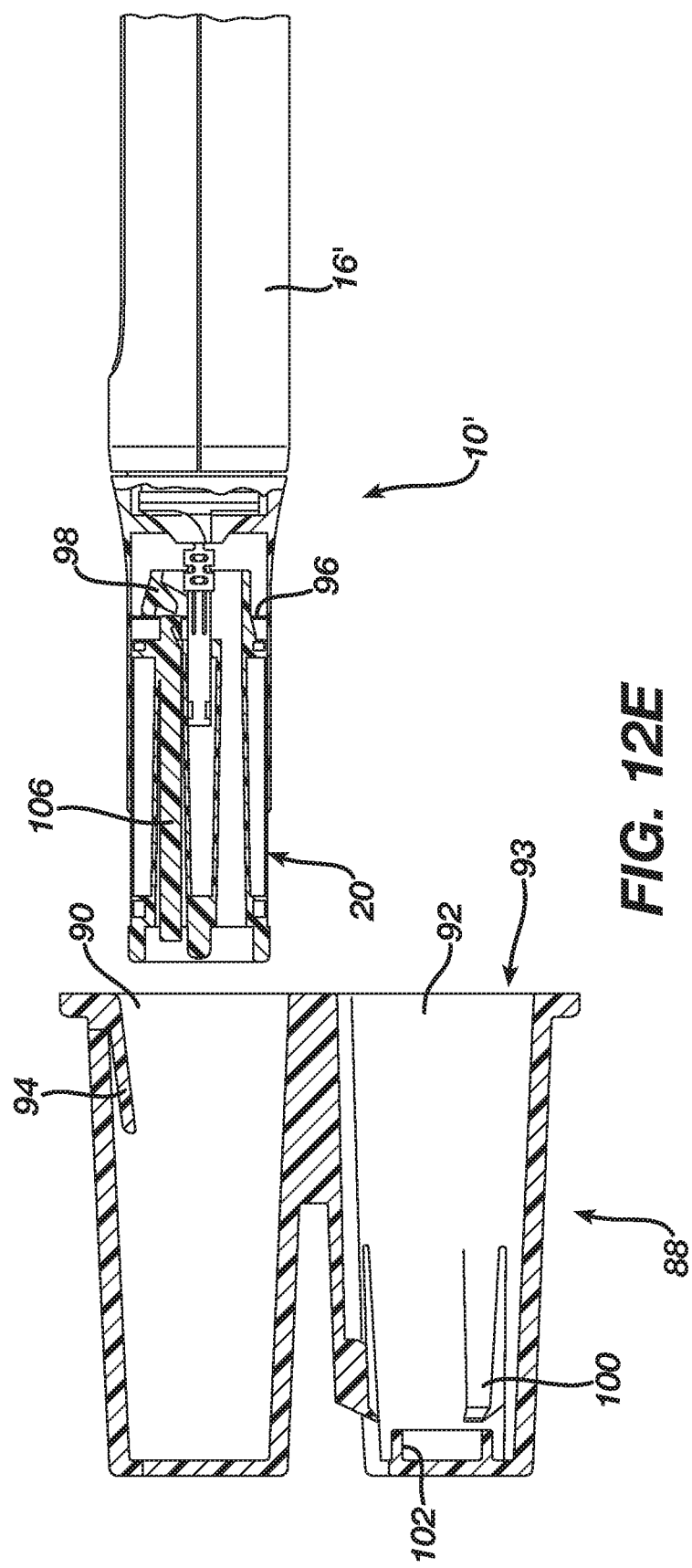

To insert an unused disposable cartridge 20 into the receptacle 18' of an ENDS 10' housing 16', the extended receptacle 18' is placed over an exposed end of the unused disposable cartridge 20. As the extended receptacle 18' is inserted into the first chamber 90 of the container 88, the outer surface of the extended receptacle 18' deflects at least one retention arm 94, which is securing the cartridge 20 in the first chamber 90, away from the unused disposable cartridge 20 (FIG. 12C). Retention arm 94 is articulable between a relaxed position extending toward the central axis of the first chamber 90 (as shown in FIG. 12B) and a flexed position disposed away from the central axis of the first chamber 90 (as shown in FIG. 12C). An inwardly-directed flange 96 disposed within the extended receptacle 18', distal the leading end thereof, guides outwardly-biased hooks 98 at the exposed end of the unused disposable cartridge 20 inwardly to permit the flange 96 to pass. Once the flange 96 has passed the unused disposable cartridge 20 hooks 98, they return outwardly to securely attach to the flange 96 of the receptacle 18' to form a fully-assembled ENDS 10' (FIG. 12D). The fully-assembled ENDS 10' is removable from the first chamber 90 of the container 88 as the retention arms 94 remain flexed outward to permit the unused disposable cartridge 20 to be removed therefrom (FIG. 12E).

Figure 13C:
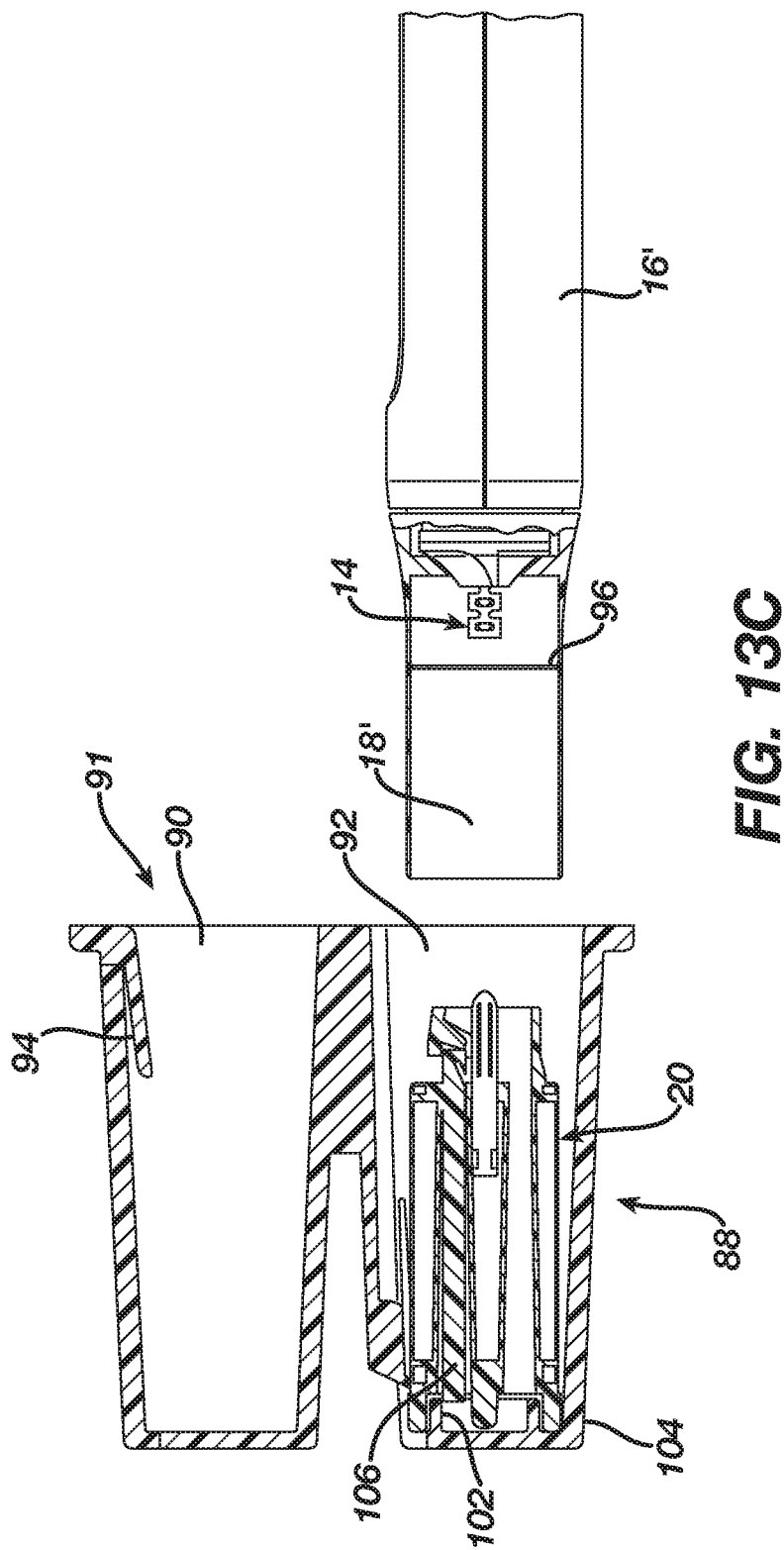

Once the ENDS 10' has been used, and the nicotine solution is consumed, the used disposable cartridge 20 can be secured into the "waste" chamber 92 for disposal. The ENDS 10' is aligned with the waste chamber 92 as shown in FIG. 13A. The used disposable cartridge 20 can be inserted into the waste chamber 92 and a set of waste chamber retention arms 100 disposed at the base of the waste chamber 92 secure the used disposable cartridge 20 in the waste chamber 92 (FIG. 13B) by engaging a lip 101 proximate the mouthpiece 24 of the used disposable cartridge 20. A projection 102 disposed at the base 104 of the waste chamber 92 also bears on one end of the transfer rod 106 to urge it away from the mouthpiece 24 to engage the outwardly-biased hooks 98 at the opposite end of the used disposable cartridge 20 and to deflect them inwardly to disengage them from the flange 96 of the receptacle 18' on the housing 16 (FIG. 13C). With the used disposable cartridge 20 securely locked in the waste chamber 92, the housing 16' can be removed from therefrom (FIG. 13C) and an unused disposable cartridge 20 can be coupled to the housing 16' for continued use.

Figure 14:
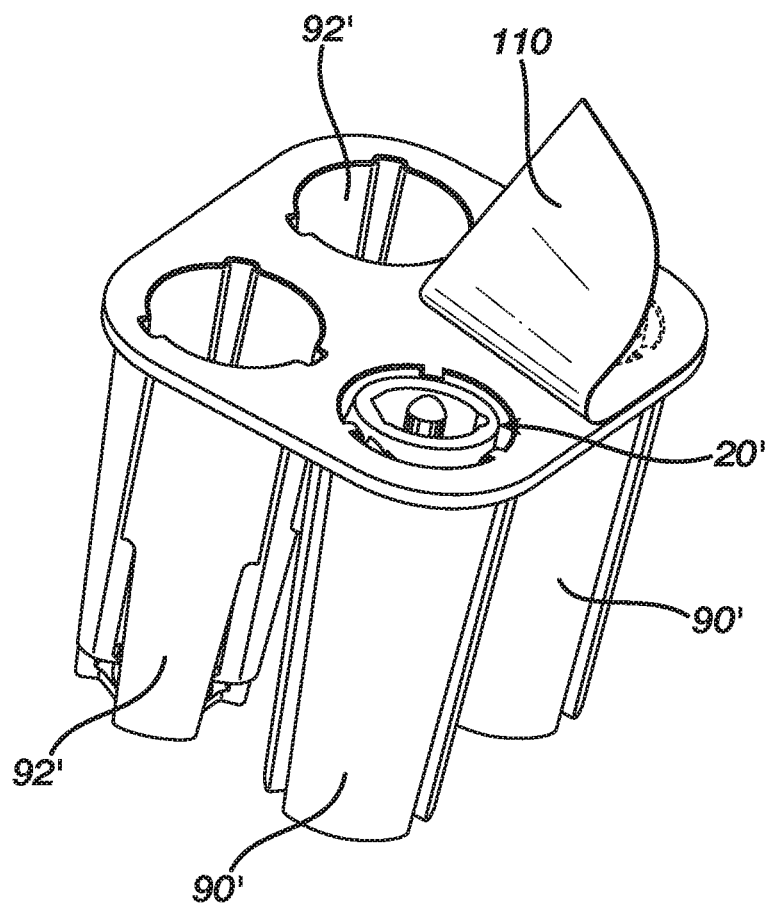
FIG. 14 is a perspective view of an alternative multichambered container.

FIG. 14 shows a preferred, multi-chambered container 108 having a plurality of first chambers 90' enclosed with a closure 110, and a plurality of waste chambers 92'. To access a first chamber 90' to acquire an unused disposable cartridge, a user would remove the closure 110 from the opening to expose the unused disposable cartridge.

Additional Alternative Embodiments

The foregoing description has generally described to a series of embodiments in which the disposable cartridge includes the mouthpiece, outlet, and reservoir, and the heater and vaporization chamber are separated from the outlet by the reservoir. Alternative embodiments may locate the heater and vaporization chamber closer to the outlet. Several of these embodiments will be described below.

Figure 15B:
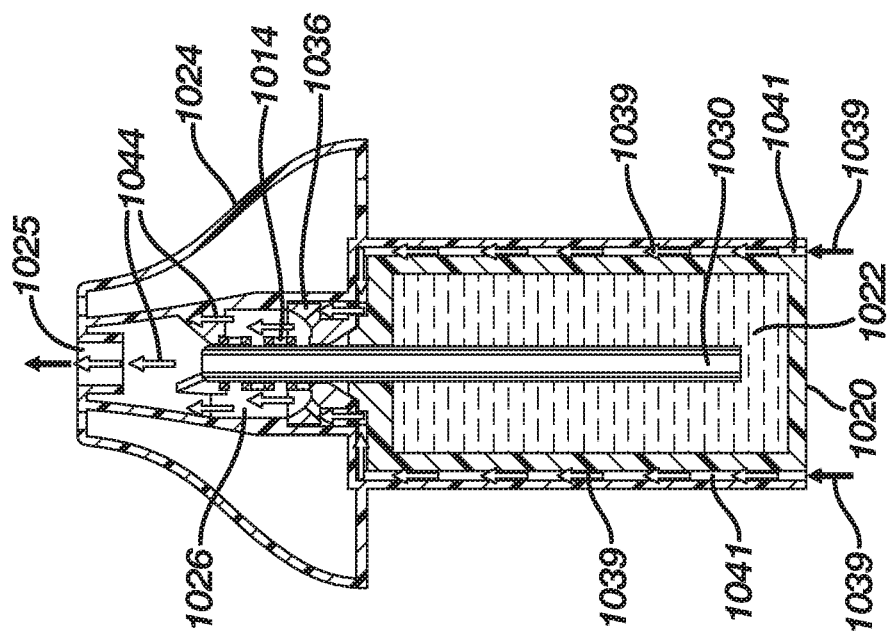
FIG. 15B is a cross-section of the mouthpiece and disposable cartridge of the ENDS of FIG. 15A.
Figure 15A:
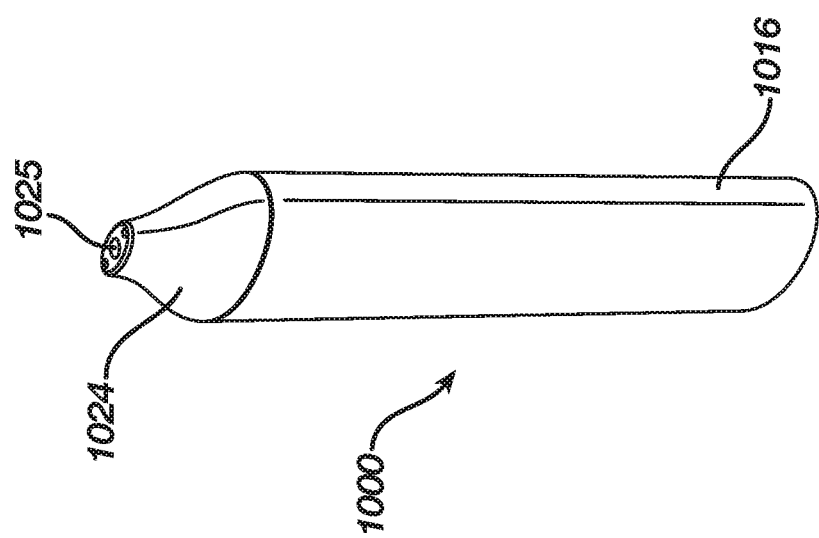
FIG. 15A is a perspective view of an alternative ENDS.

In one embodiment shown in FIGS. 15A and B, the ENDS 1000 includes a housing 1016 containing a power source (not shown) and one or more air inlets (not shown); a reusable mouthpiece 1024 including an electric heater 1014, an air outlet 1025 and a vaporization chamber 1026; an elongate wick 1030; and a disposable cartridge 1020 containing a reservoir 1022. The reusable mouthpiece 1024 is removably attachable to the housing 1016 to permit a disposable cartridge 1020 to be placed in the ENDS 1000. One of ordinary skill in the art will recognize that ENDS 1000 will require an electrical circuit between the electric heater 1014 (contained in the mouthpiece 1024) and the power source (contained in the housing 1016). Therefore, a releasable electrical connection (not shown) is required between the housing 1016 and the mouthpiece 1024. In this embodiment, the electric heater 1014 is mounted on a base plate 1036, and the base plate 1036 is disposed in facing relation to the disposable cartridge 1020, when assembled. Thus, in the assembled ENDS 1000, the wick 1030 extends from the reservoir 1022, through the base plate 1036, and into the electric heater 1014. In use, inlet air 1039 enters the ENDS 1000 through air inlets (not shown) and passes through one or more internal conduits 1041 to one or more air passages 1052 through the base plate 1036 into the vaporization chamber 1026 where it forms the nicotine aerosol 1044, as described above. The nicotine aerosol 1044 can then be withdrawn from the air outlet 1025 in the reusable mouthpiece 1024.

Figures 16A, 16B:
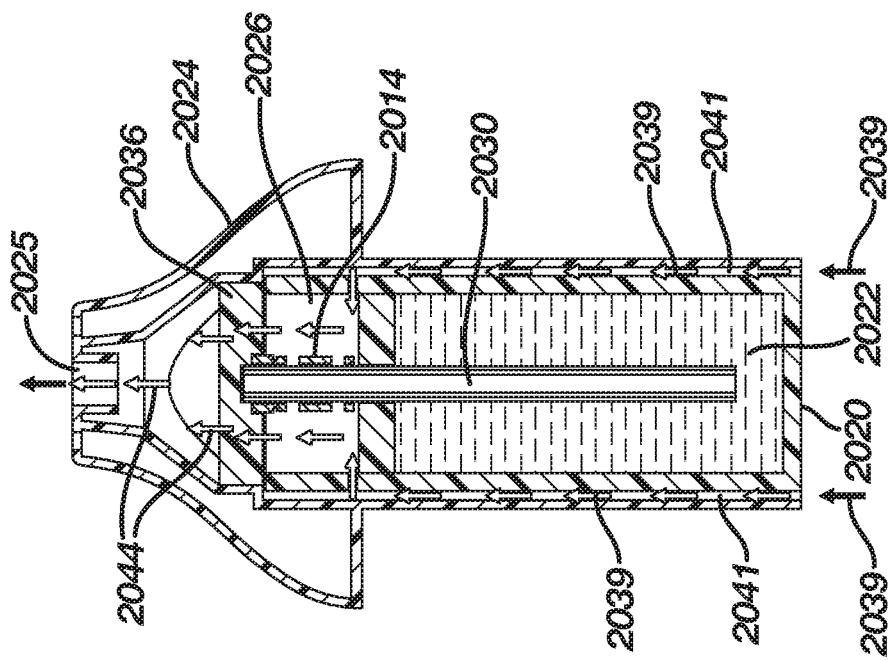
FIG. 16A is a perspective view of an alternative ENDS.
FIG. 16B is a cross-section of the mouthpiece and disposable cartridge of the ENDS of FIG. 16A.

In one embodiment shown in FIGS. 16A and B, the ENDS 2000 includes a housing 2016 containing a power source (not shown) and one or more air inlets (not shown); a reusable mouthpiece 2024 including an electric heater 2014 and an air outlet 2025; a vaporization chamber 2026; an elongate wick 2030; and a disposable cartridge 2020 containing a reservoir 2022. The reusable mouthpiece 2024 is removably attachable to the housing 2016 to permit a disposable cartridge 2020 to be placed in the ENDS 2000. The removable mouthpiece 2024, the disposable cartridge 2020 and the base plate 2036 form the vaporization chamber 2026 in the assembled ENDS 2000. One of ordinary skill in the art will recognize that ENDS 2000 will require an electrical circuit between the electric heater 2014 (contained in the mouthpiece 2024) and the power source (contained in the housing 2016). Therefore, a releasable electrical connection (not shown) is required between the housing 2016 and the mouthpiece 2024. In this embodiment, the electric heater 2014 is mounted on a base plate 2036, and the electric heater 2014 is disposed in facing relation to the disposable cartridge 2020, when assembled. Thus, in the assembled ENDS 2000, the wick 2030 extends from the reservoir 2022 and into the electric heater 2014. In use, inlet air 2039 enters the ENDS 2000 through air inlets (not shown) and passes through one or more internal conduits 2041 to the vaporization chamber 2026 where it forms the nicotine aerosol 2044, as described above. The nicotine aerosol 2044 can then be withdrawn through one or more air passages (not shown) through the base plate 2036 and the air outlet 2025 in the reusable mouthpiece 2024.

Figure 17B:
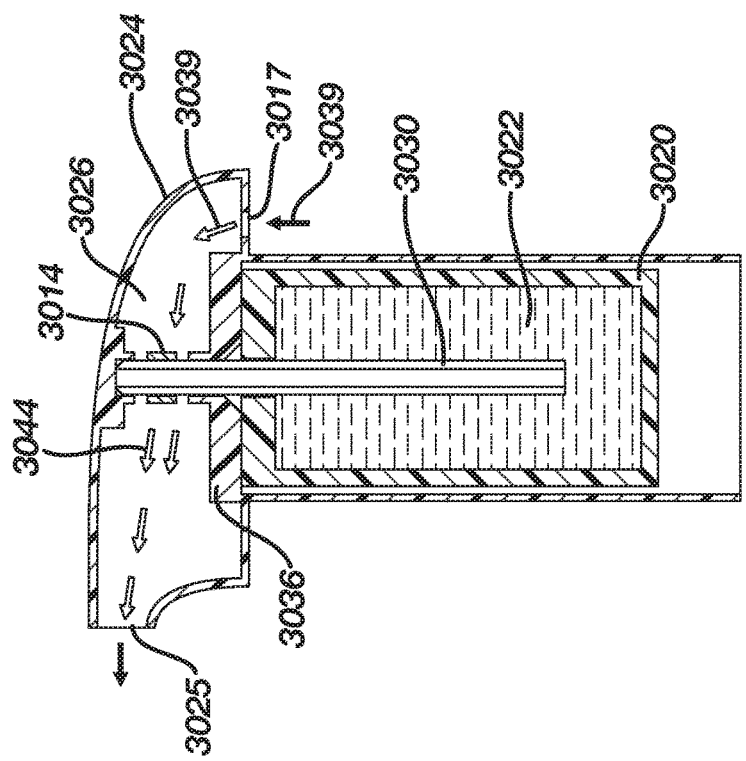
FIG. 17B is a cross-section of the mouthpiece and disposable cartridge of the ENDS of FIG. 17A.
Figure 17A:
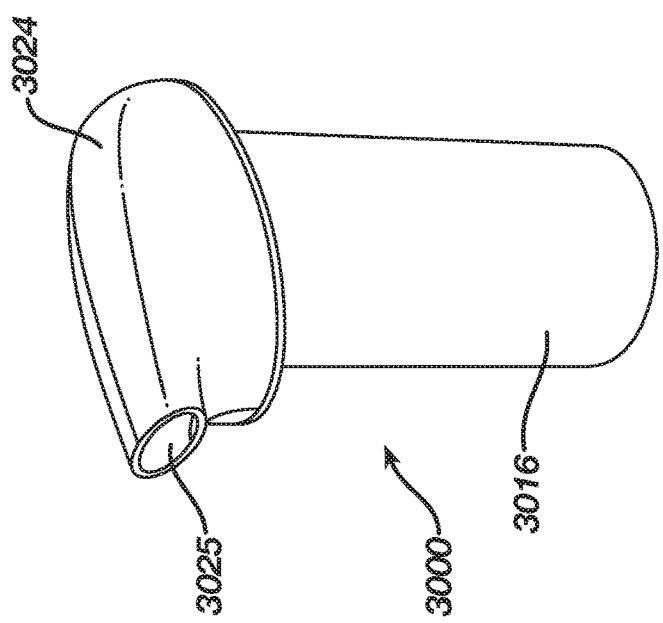
FIG. 17A is a perspective view of an alternative ENDS.

In one embodiment shown in FIGS. 17A and B, the ENDS 3000 includes a housing 3016 containing a power source (not shown); a reusable mouthpiece 3024 including an electric heater 3014, one or more air inlets 3017, an air outlet 3025 and a vaporization chamber 3026; an elongate wick 3030; and a disposable cartridge 3020 containing a reservoir 3022. The reusable mouthpiece 3024 is removably attachable to the housing 3016 to permit a disposable cartridge 3020 to be placed in the ENDS 3000. One of ordinary skill in the art will recognize that ENDS 3000 will require an electrical circuit between the electric heater 3014 (contained in the mouthpiece 3024) and the power source (contained in the housing 3016). Therefore, a releasable electrical connection (not shown) is required between the housing 3016 and the mouthpiece 3024. In this embodiment, the electric heater 3014 is mounted on a base plate 3036, and the base plate 3036 is disposed in facing relation to the disposable cartridge 3020, when assembled. Thus, in the assembled ENDS 3000, the wick 3030 extends from the reservoir 3022, through the base plate 3036, and into the electric heater 3014. In use, inlet air 3039 enters the ENDS 3000 through air inlets 3017 and enters the vaporization chamber 3026 perpendicular to the length of the heater where it forms the nicotine aerosol 3044, as described above. In this embodiment, the air/nicotine aerosol flow is perpendicular to the orientation of the electric heater 3014. The nicotine aerosol 3044 can then be withdrawn from the air outlet 3025 in the reusable mouthpiece 3024.

Figure 18B:
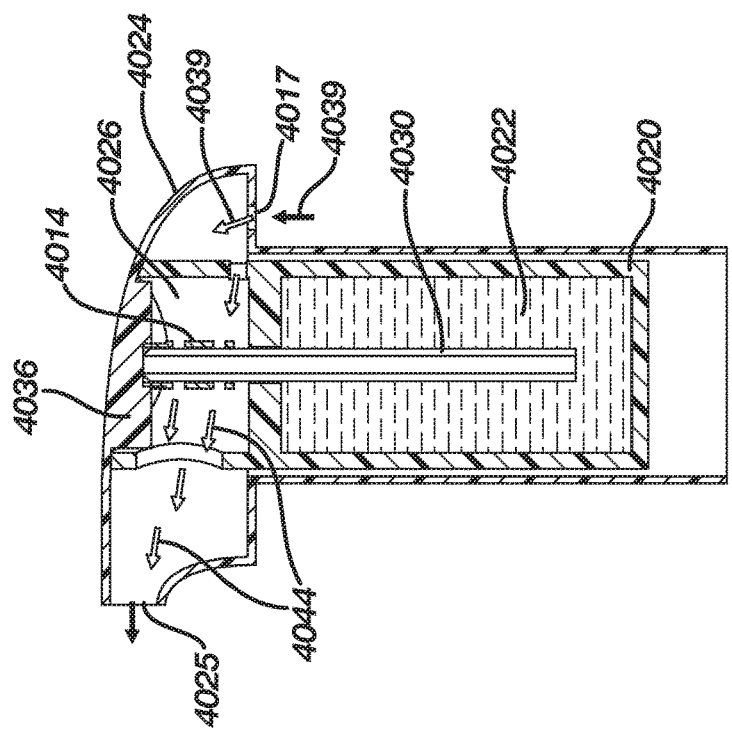
FIG. 18B is a cross-section of the mouthpiece and disposable cartridge of the ENDS of FIG. 18A.
Figure 18A:
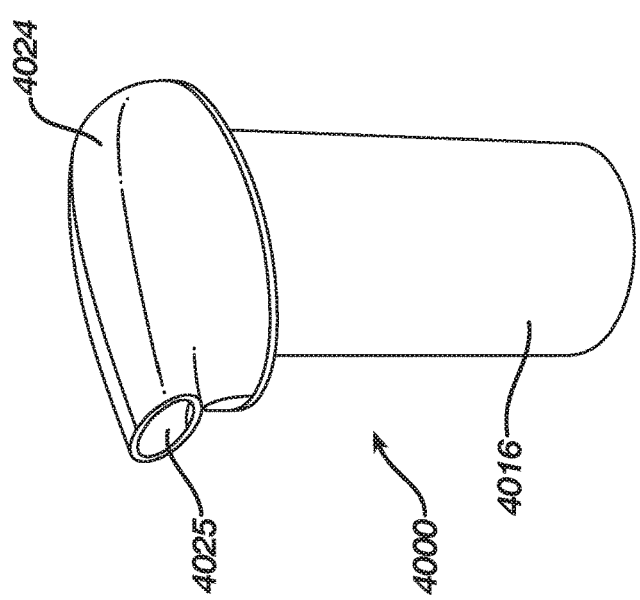
FIG. 18A is a perspective view of an alternative ENDS.

In one embodiment shown in FIGS. 18A and B, the ENDS 4000 includes a housing 4016 containing a power source (not shown); a reusable mouthpiece 4024 including an electric heater 4014, one or more air inlets 4017, and an air outlet 4025; a vaporization chamber 4026; an elongate wick 4030; and a disposable cartridge 4020 containing a reservoir 4022. The reusable mouthpiece 4024 is removably attachable to the housing 4016 to permit a disposable cartridge 4020 to be placed in the ENDS 4000. The removable mouthpiece 4024, the disposable cartridge 4020 and the base plate 4036 form the vaporization chamber 4026 in the assembled ENDS 4000. One of ordinary skill in the art will recognize that ENDS 4000 will require an electrical circuit between the electric heater 4014 (contained in the mouthpiece 4024) and the power source (contained in the housing 4016). Therefore, a releasable electrical connection (not shown) is required between the housing 4016 and the mouthpiece 4024. In this embodiment, the electric heater 4014 is mounted on a base plate 4036, and the electric heater 4014 is disposed in facing relation to the disposable cartridge 4020, when assembled. Thus, in the assembled ENDS 4000, the wick 4030 extends from the reservoir 4022 and into the electric heater 4014. In use, inlet air 4039 enters the ENDS 4000 through air inlets 4017 and enters the vaporization chamber 4026 perpendicular to the length of the heater where it forms the nicotine aerosol 4044, as described above. In this embodiment, the air/nicotine aerosol flow is perpendicular to the orientation of the electric heater 4014. The nicotine aerosol 4044 can then be withdrawn from the air outlet 4025 in the reusable mouthpiece 4024.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. An electronic nicotine delivery system comprising:
   (a) a housing, the housing having at least one air inlet and providing a receptacle for securing a disposable cartridge;
   (b) an electric heater contained within the housing; and
   (c) the disposable cartridge is configured to be securely locked into the receptacle, the disposable cartridge comprising:
      (i) a reservoir containing a nicotine-containing liquid;
      (ii) a port in liquid communication with the reservoir; and
      (iii) a liquid barrier disposed proximate the port to prevent undesired leakage of the nicotine-containing liquid from the reservoir; and
      (iv) a durable, elongate wick, slidably fitted in the port, adjacent the barrier;
   wherein during the locking of the disposable cartridge into the receptacle, the durable elongate wick slides further into the reservoir to rupture the barrier to provide a liquid conduit from the reservoir to the electric heater.

2. The electronic nicotine delivery system according to claim 1, further comprising an open mouthpiece disposed distal the port and at least one outlet conduit operatively connected to the mouthpiece and extending to a location proximate the port.

3. The electronic nicotine delivery system according to claim 1, wherein the liquid barrier is disposed about one end of the durable, elongate wick.

4. The electronic nicotine delivery system according to claim 1, wherein the durable, elongate wick is slidable into the electric heater in the electronic nicotine delivery system.

5. The electronic nicotine delivery system according to claim 1, wherein the durable, elongate wick has substantially non-porous support and a capillary structure on an outer surface thereof.

6. The electronic nicotine delivery system according to claim 1, wherein the durable, elongate wick has substantially non-porous tubular support and a capillary structure on an outer surface thereof.

7. The electronic nicotine delivery system according to claim 1, wherein, when assembled, the housing, the electric heater, and disposable cartridge cooperate to form a vaporization chamber within the housing proximate the electric heater, wherein the electric heater vaporizes nicotine-containing liquid transported from the reservoir by the durable, elongate wick in the vaporization chamber.

* * * * *